(12) United States Patent
Lintner et al.

(10) Patent No.: US 8,404,648 B2
(45) Date of Patent: Mar. 26, 2013

(54) POLYPEPTIDES KXK AND THEIR USE

(75) Inventors: Karl Lintner, Rambouillet (FR); Olivier Peschard, Saint-Priest (FR); Philippe Mondon, Paris (FR); Claire Mas Chamberlin, Chevreuse (FR)

(73) Assignee: Sederma (FR)

( * ) Notice: Subject to any disclaimer, the term of this patent is extended or adjusted under 35 U.S.C. 154(b) by 727 days.

(21) Appl. No.: 12/224,032

(22) PCT Filed: Feb. 16, 2006

(86) PCT No.: PCT/IB2006/001436
§ 371 (c)(1),
(2), (4) Date: Dec. 2, 2009

(87) PCT Pub. No.: WO2007/093839
PCT Pub. Date: Aug. 23, 2007

(65) Prior Publication Data
US 2011/0033507 A1  Feb. 10, 2011

(51) Int. Cl.
*A61K 38/07* (2006.01)
*A61P 17/00* (2006.01)

(52) U.S. Cl. ...................... 514/21.9; 514/18.8
(58) Field of Classification Search .................. None
See application file for complete search history.

(56) References Cited

U.S. PATENT DOCUMENTS

| | | |
|---|---|---|
| 1,985,424 A | 12/1934 | Piggott |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,703,798 A | 3/1955 | Schwartz |
| 2,798,053 A | 7/1957 | Brown |
| 2,809,971 A | 10/1957 | Bernstein |
| 2,826,551 A | 3/1958 | Geen |
| 2,965,576 A | 12/1960 | Wilson |
| 3,155,591 A | 11/1964 | Hilfer |
| 3,236,733 A | 2/1966 | Karsten et al. |
| 3,332,880 A | 7/1967 | Kesller et al. |
| 3,753,196 A | 8/1973 | Kurtz et al. |
| 3,755,560 A | 8/1973 | Dickert et al. |
| 3,761,418 A | 9/1973 | Parran, Jr. et al. |
| 3,929,678 A | 12/1975 | Laughlin et al. |
| 3,958,581 A | 5/1976 | Abegg et al. |
| 3,959,461 A | 5/1976 | Bailey et al. |
| 3,962,418 A | 6/1976 | Birkofer |
| 3,964,500 A | 6/1976 | Drakoff |
| 4,152,416 A | 5/1979 | Spitzer et al. |
| 4,202,879 A | 5/1980 | Shelton |
| 4,323,683 A | 4/1982 | Bolich, Jr. et al. |
| 4,345,080 A | 8/1982 | Bolich, Jr. |
| 4,364,837 A | 12/1982 | Pader |
| 4,379,753 A | 4/1983 | Bolich, Jr. |
| 4,387,090 A | 6/1983 | Bolich, Jr. |
| 4,421,769 A | 12/1983 | Dixon et al. |
| 4,470,982 A | 9/1984 | Winkler |
| 4,509,949 A | 4/1985 | Huang et al. |
| 4,557,853 A | 12/1985 | Collins |
| 4,599,379 A | 7/1986 | Flesher et al. |
| 4,628,078 A | 12/1986 | Glover et al. |
| 4,677,120 A | 6/1987 | Parish et al. |
| 4,741,855 A | 5/1988 | Grote et al. |
| 4,800,197 A | 1/1989 | Kowcz et al. |
| 4,816,261 A | 3/1989 | Luebbe et al. |
| 4,835,206 A | 5/1989 | Farrar et al. |

(Continued)

FOREIGN PATENT DOCUMENTS

| | | |
|---|---|---|
| EP | 0 228 868 A2 | 7/1987 |
| EP | 0 330 369 A1 | 8/1989 |
| EP | 0218773 A1 | 12/1992 |
| EP | 0518772 A1 | 12/1992 |
| FR | 2654619 A1 | 5/1991 |
| FR | 2694195 A1 | 2/1994 |
| FR | 2702766 A1 | 9/1994 |
| FR | 2 732 215 A1 | 10/1996 |
| FR | 2733149 A1 | 10/1996 |
| FR | 2 769 502 A1 | 4/1999 |
| FR | 2771002 A1 | 5/1999 |
| FR | 2781231 A1 | 1/2000 |
| FR | 2788058 A1 | 7/2000 |
| FR | 2854897 A1 | 11/2004 |
| FR | 2855057 A1 | 11/2004 |

(Continued)

OTHER PUBLICATIONS

Backers et al., "Synthesis of positional-scanning libraries of fluorogenic peptides substrates to define the extended substrate specificity of plasmin and thrombin", Nature Biotechnology, Nature Publishing Group, vol. 18, pp. 197-193, New York, NY Feb. 2000.
Katayama et al., "A Pentapeptide from Type I Procollagen Promotes Extracellular Matrix Production", Communication, The Journal of Biological Chemistry, vol. 268, No. 14, pp. 9941-9944, 1993.

*Primary Examiner* — Cecilia J Tsang
*Assistant Examiner* — Ronald Niebauer
(74) *Attorney, Agent, or Firm* — Lerner, David, Littenberg, Krumholz & Mentlik, LLP

(57) ABSTRACT

The invention concerns polypeptides of the general formula (I): A-(Xaa)$_n$-Lys-X-Lys-B wherein: i) A is —NH2, NH3+, or NH-D (D is an acyl group being biotin or an alkyl chain (C2-C22)), H) B is H, O$^-$OR$^1$ or NR$^2$R$^3$ and R$^1$, R$^2$ and R$^3$ independently either: H or an alkyl chain (C1-C24), iii) (Xaa)$_n$ is an amino acid chain including any amino acid natural or not, excluding arginine and lysine, iv) "n" is between 0-3, and v) X is either a chain of two any amino acids (Xaa1Xaa2) which may be the same or different, excluding arginine, lysine and excluding Xaa1Xaa2=Thr-Thr, Gly-His and Glu-His, or X is a spacer selected among beta-alanyl, 5-amino-valeroyl, 4-amino-cyclohexanoyl, 4-amino-butyroyl, 6-amino-caproyl and derivatives thereof. More particularly, the invention concerns polypeptides of formula (I) wherein "n" is 0 and with the formula: A-Lys-X-Lys-B; A, X and B being defined herein. Compositions containing at least one of said polypeptides and their use.

7 Claims, No Drawings

U.S. PATENT DOCUMENTS

| | | |
|---|---|---|
| 4,847,071 A | 7/1989 | Bissett et al. |
| 4,849,484 A | 7/1989 | Heard |
| 4,885,311 A | 12/1989 | Parish et al. |
| 4,960,764 A | 10/1990 | Figueroa, Jr. et al. |
| 4,970,252 A | 11/1990 | Sakuta et al. |
| 4,976,953 A | 12/1990 | Orr et al. |
| 5,011,681 A | 4/1991 | Ciotti et al. |
| 5,049,584 A | 9/1991 | Purcell et al. |
| 5,073,371 A | 12/1991 | Turner et al. |
| 5,073,372 A | 12/1991 | Turner et al. |
| 5,087,445 A | 2/1992 | Haffey et al. |
| 5,100,660 A | 3/1992 | Hawe et al. |
| 5,104,646 A | 4/1992 | Bolich, Jr. et al. |
| 5,106,609 A | 4/1992 | Bolich, Jr. et al. |
| 5,120,532 A | 6/1992 | Wells et al. |
| 5,124,356 A | 6/1992 | Purcell et al. |
| RE34,075 E | 9/1992 | Purcell et al. |
| 5,151,209 A | 9/1992 | McCall et al. |
| 5,151,210 A | 9/1992 | Steuri et al. |
| RE34,584 E | 4/1994 | Grote et al. |
| 5,312,832 A * | 5/1994 | Chan .......................... 524/513 |
| 5,412,004 A | 5/1995 | Tachibana et al. |
| 5,487,884 A | 1/1996 | Bissett et al. |
| 5,607,980 A | 3/1997 | McAtee et al. |
| 5,652,228 A | 7/1997 | Bissett |
| 5,654,362 A | 8/1997 | Schulz, Jr. et al. |
| 5,681,852 A | 10/1997 | Bissett |
| 5,760,116 A | 6/1998 | Kilgour et al. |
| 5,811,487 A | 9/1998 | Schulz, Jr. et al. |
| 5,837,793 A | 11/1998 | Harashima et al. |
| 5,939,082 A | 8/1999 | Oblong et al. |
| 6,068,834 A | 5/2000 | Kvalnes et al. |
| 6,159,485 A | 12/2000 | Yu et al. |
| 6,190,645 B1 | 2/2001 | SaNogueira et al. |
| 6,372,717 B1 | 4/2002 | Greff |
| 6,489,446 B1 * | 12/2002 | Rothstein et al. ............. 530/353 |
| 6,620,419 B1 | 9/2003 | Lintner |
| 2004/0013667 A1 | 1/2004 | Kelsey et al. |
| 2004/0120918 A1 | 6/2004 | Lintner et al. |
| 2004/0132667 A1 | 7/2004 | Lintner |
| 2006/0067905 A1 | 3/2006 | Lintner et al. |

FOREIGN PATENT DOCUMENTS

| | | |
|---|---|---|
| GB | 849 433 A | 9/1960 |
| GB | 2 274 585 A | 8/1994 |
| WO | 91/16035 | 10/1991 |
| WO | 93/23028 A1 | 11/1993 |
| WO | 95/34280 A1 | 12/1995 |
| WO | 96/33689 A1 | 10/1996 |
| WO | 97/05856 A1 | 2/1997 |
| WO | 98/05299 A1 | 2/1998 |
| WO | 98/07744 A1 | 2/1998 |
| WO | 98/43607 A1 | 10/1998 |
| WO | 99/18927 A1 | 4/1999 |
| WO | 99/25369 A1 | 5/1999 |
| WO | 9940897 A1 | 8/1999 |
| WO | 00/15188 A1 | 3/2000 |
| WO | 00/40611 A1 | 7/2000 |
| WO | 00/43417 A1 | 7/2000 |
| WO | 00/58347 A1 | 10/2000 |
| WO | WO-01/31019 A2 | 5/2001 |
| WO | 01/43701 A2 | 6/2001 |
| WO | 01/62218 A1 | 8/2001 |
| WO | 01/64178 A1 | 9/2001 |
| WO | 02/15871 A1 | 2/2002 |
| WO | 02/076423 A2 | 10/2002 |
| WO | 03/017966 A2 | 3/2003 |
| WO | 03/028692 A2 | 4/2003 |
| WO | 03/068141 A2 | 8/2003 |
| WO | 2004012650 A2 | 2/2004 |
| WO | 2004/024695 A1 | 3/2004 |

\* cited by examiner

SEQUENCE LISTING

```
<160> NUMBER OF SEQ ID NOS: 16

<210> SEQ ID NO 1
<211> LENGTH: 5
<212> TYPE: PRT
<213> ORGANISM: artificial sequence
<220> FEATURE:
<223> OTHER INFORMATION: synthetic peptide

<400> SEQUENCE: 1

Lys Thr Thr Lys Ser
1               5

<210> SEQ ID NO 2
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, Pal (C16). Sequence description:
      palmitoyl-KTTKS

<400> SEQUENCE: 2

Lys Thr Thr Lys Ser
1               5

<210> SEQ ID NO 3
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, palmitoyl (C16). sequence:
      Pal-Val-Gly-Val-Ala-Pro-Gly

<400> SEQUENCE: 3

Val Gly Val Ala Pro Gly
1               5

<210> SEQ ID NO 4
<211> LENGTH: 7
<212> TYPE: PRT
<213> ORGANISM: Artificial
```

```
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, A with A = -NH2, NH3+, NH-D (D= Acyl
      being biotin or an alkyl chain from C2 to C22, linear, branched
      or cyclic, substituted or not, saturated or not, hydroxylated or
      not sulfurated or not)
<220> FEATURE:
<221> NAME/KEY: MOD_RES
<222> LOCATION: (1)..(3)
<223> OTHER INFORMATION: variable amino acid natural or non natural;
      excluding Arg and Lys. This region may encompass 0-3 amino acids,
      which may be the same or different.
<220> FEATURE:
<221> NAME/KEY: MOD_RES
<222> LOCATION: (5)..(6)
<223> OTHER INFORMATION: chain of 2 amino acids natural or non natural
      (Xaa1Xaa2) which may be the same or different (excluding Arg, Lys
      and Xaa1Xaa2 = Thr-Thr, Gly-His,and Glu-His)
<220> FEATURE:
<221> NAME/KEY: MOD_RES
<222> LOCATION: (7)..(7)
<223> OTHER INFORMATION: B = H, O-, OR1 or NR2R3 and R1, R2 and R3
      independently H, or an alkyl chain of from C1 to C24, linear,
      branched or cyclic, substituted or not, saturated or not,
      hydroxylated or not, sulfurated or not; sequence:
      A-Xaa-Xaa-Xaa-Lys-Xaa1-Xaa2-Lys-B

<400> SEQUENCE: 4

Xaa Xaa Xaa Lys Xaa Xaa Lys
1               5

<210> SEQ ID NO 5
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, A with A = -NH2, NH3+, NH-D (D= Acyl
      being biotin or an alkyl chain from C2 to C22, linear, branched or
      cyclic, substituted or not, saturated or not, hydroxylated or not
      sulfurated or not)
<220> FEATURE:
<221> NAME/KEY: MOD_RES
<222> LOCATION: (1)..(3)
<223> OTHER INFORMATION: variable amino acid natural or non natural;
      excluding Arg and Lys. This region may encompass 0-3 amino acids,
      which may be the same or different.
<220> FEATURE:
<221> NAME/KEY: MOD_RES
<222> LOCATION: (5)..(5)
<223> OTHER INFORMATION: X is a spacer = beta-alanyl, 5-amino-valeroyl,
      4-amino-cyclohexanoyl, 4-amino-butyroyl, 6-amino-caproyl or
      derivatives thereof, wherein the carbon chain may be substituted
      or not, saturated or not, hydroxylated or not, sulfurated or not
<220> FEATURE:
<221> NAME/KEY: MOD_RES
<222> LOCATION: (6)..(6)
<223> OTHER INFORMATION: B = H, O-, OR1 or NR2R3 and R1, R2 and R3
      independently H , or an alkyl chain of from C1 to C24, linear,
      branched or cyclic, substituted or not, saturated or not,
      hydroxylated or not, sulfurated or not; sequence:
      A-Xaa-Xaa-Xaa-Lys-X-Lys-B.

<400> SEQUENCE: 5

Xaa Xaa Xaa Lys Xaa Lys
1               5
```

```
<210> SEQ ID NO 6
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, A with A = -NH2, NH3+, NH-D (D= Acyl
      being biotin or an alkyl chain from C2 to C22, linear, branched or
      cyclic, substituted or not, saturated or not, hydroxylated or not
      sulfurated or not)
<220> FEATURE:
<221> NAME/KEY: MOD_RES
<222> LOCATION: (2)..(3)
<223> OTHER INFORMATION: chain of 2 amino acids natural or non natural
      (Xaa1Xaa2) which may be the same or different (excluding Arg, Lys
      and Xaa1Xaa2 = Thr-Thr, Gly-His,and Glu-His)
<220> FEATURE:
<221> NAME/KEY: MOD_RES
<222> LOCATION: (4)..(4)
<223> OTHER INFORMATION: B = H, O-, OR1 or NR2R3 and R1, R2 and R3
      independently H, or an alkyl chain of from C1 to C24, linear,
      branched or cyclic, substituted or not, saturated or not,
      hydroxylated or not, sulfurated or not; sequence:
      A-Lys-Xaa1-Xaa2-Lys-B.

<400> SEQUENCE: 6

Lys Xaa Xaa Lys
1

<210> SEQ ID NO 7
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, palmitoyl (C16). sequence:
      Pal-Lys-Thr-Phe-Lys

<400> SEQUENCE: 7

Lys Thr Phe Lys
1

<210> SEQ ID NO 8
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, elaidoyl (C18).sequence:
      Elaidoyl-Lys-Thr-Phe-Lys

<400> SEQUENCE: 8

Lys Thr Phe Lys
1

<210> SEQ ID NO 9
<211> LENGTH: 4
<212> TYPE: PRT
<213> ORGANISM: Artificial
<220> FEATURE:
<223> OTHER INFORMATION: Synthetic Peptide
```

```
<220> FEATURE:
<221> NAME/KEY: MOD_RES
<222> LOCATION: (1)..(1)
<223> OTHER INFORMATION: AMIDATION, elaidoyl (C18).sequence:
      Elaidoyl-Lys-Thr-Ala-Lys

<400> SEQUENCE: 9

Lys Thr Ala Lys
1

<210> SEQ ID NO 10
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, elaidoyl (C18).sequence:
      Elaidoyl-Lys-Ala-Tyr-Lys

<400> SEQUENCE: 10

Lys Ala Tyr Lys
1

<210> SEQ ID NO 11
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, elaidoyl (C18).sequence:
      Elaidoyl-Lys-Phe-Tyr-Lys

<400> SEQUENCE: 11

Lys Phe Tyr Lys
1

<210> SEQ ID NO 12
<211> LENGTH: 4
<212> TYPE: PRT
<213> ORGANISM: artificial sequence
<220> FEATURE:
<223> OTHER INFORMATION: synthetic peptide

<400> SEQUENCE: 12

Arg Ser Arg Lys
1

<210> SEQ ID NO 13
<211> LENGTH: 4
<212> TYPE: PRT
<213> ORGANISM: artificial sequence
<220> FEATURE:
<223> OTHER INFORMATION: synthetic peptide

<400> SEQUENCE: 13

Gly Gln Pro Arg
1

<210> SEQ ID NO 14
<211> LENGTH: 6
<212> TYPE: PRT
<213> ORGANISM: artificial sequence
<220> FEATURE:
<223> OTHER INFORMATION: synthetic peptide
```

```
<400> SEQUENCE: 14

Val Gly Val Ala Pro Gly
1               5

<210> SEQ ID NO 15
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: AMIDATION, palmitoyl (C16). sequence:
      Pal-Gly-Gln-Pro-Arg

<400> SEQUENCE: 15

Gly Gln Pro Arg
1

<210> SEQ ID NO 16
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, palmitoyl (C16). sequence:
      Pal-Tyr-Gly-Gly-Phe-X
<220> FEATURE:
<221> NAME/KEY: MOD_RES
<222> LOCATION: (5)..(5)
<223> OTHER INFORMATION: Xaa is a Met or a Leu aminoacid

<400> SEQUENCE: 16

Tyr Gly Gly Phe Xaa
1               5
```

POLYPEPTIDES KXK AND THEIR USE

BACKGROUND OF THE INVENTION

Our skin is the first image each of us offers to those who behold us. From time immemorial, the appearance of the skin has been a subject of preoccupation.

Our current knowledge of the physiology of the skin now enables us to propose cosmetic solutions to the various dysfunctions induced by external aggression and aging. However, many things remain poorly elucidated, poorly understood and poorly controlled.

This is true, for instance, in the case of the general symptoms of cutaneous aging, which give rise to wrinkles and flaccid and thin skin. The treatment of those symptoms is an important subject of research for the cosmetic market.

External or internal factors can both lead to the emergence of symptoms of aging. Moreover, as skin ages, the synthesis of collagen or other macromolecules in connective tissue is slowed; proteolysis, induced by solar radiation, is accelerated and the skin grows thinner and loses elasticity.

Numerous cosmetic compositions intended to improve the appearance of facial skin have been proposed to date. These include moisturizing products, anti-wrinkle creams and smoothing and soothing lotions. Frequently, however, those products have side effects, are associated with stability problems and/or do not make good their promise over time. This is, in particular, the case for formulae containing vitamins and plant extracts.

The present invention is designed to assist in resolving the aesthetic problems posed by those aging symptoms and, preferably, to address the underlying problems.

Katayama et al. (The Journal of Biological Chemistry, Vol. 268, No. 14, pages 9941-9944, 1993) found that the minimal subfragment sequence for stimulating collagen and fibronectin is represented by the pentapeptide Lys-Thr-Thr-Lys-Ser (SEQ ID NO: 1). Sequences with four amino acids or less have a slighter or no stimulating effect. U.S. Pat. No. 6,620, 419 discloses the effect of the palmitoylated pentapeptide Pal-Lys-Thr-Thr-Lys-Ser (SEQ ID NO: 2) as a component for treating skin aging, accelerating wound healing and improving skin moisturizing.

SEDERMA sells a product under the trade name BIOPEPTIDE EL™, which includes Palmitoyl-Val-Gly-Val-Ala-Pro-Gly (SEQ ID NO: 3), which is used for helping restore the suppleness and firmness of skin, but not for treating wrinkles and N-Palmitoyl-Lys-Thr-Thr-Lys-Ser (SEQ ID NO: 2) under the trade name MATRIXYL.

SUMMARY OF THE INVENTION

It has now been found, surprisingly, that new polypeptides and derivatives, and more particularly new tetrapeptides and tripeptides are highly pharmaceutically and/or cosmetically effective and are particularly appropriate for use in dermopharmaceutically and/or cosmetically effective compositions.

The present invention therefore relates to a polypeptide of the general formula (I): A-(Xaa)$_n$-Lys-X-Lys-B wherein: A is —NH2, NH3+, or NH-D, D is an acyl group being biotin or an alkyl chain from 2 to 22 carbons, linear, or branched or cyclic, substituted or unsubstituted, saturated or unsaturated, hydroxylated or non-hydroxylated, sulfurated or non-sulfurated, wherein B is H, O$^-$, OR1 or NR2R3 and R1, R2 and R3 independently either: a hydrogen atom, or an alkyl chain of from 1 to 24 carbons, linear, branched or cyclic, substituted or unsubstituted, saturated or unsaturated, hydroxylated or non-hydroxylated, sulfurated or non-sulfurated, wherein (Xaa)n is an amino acid chain and (Xaa) is any amino acid natural or non natural excluding arginine and lysine, "n" is between 0 and 3, and wherein X is either a chain of two any amino acids (Xaa1Xaa2) natural or non natural, which may be the same or different excluding arginine and lysine and excluding Xaa1Xaa2 being Thr-Thr, Gly-His and Glu-His (SEQ ID NO: 4) or X is a spacer selected among the group comprising beta-alanyl, 5-amino-valeroyl, 4-amino-cyclohexanoyl, 4-amino-butyroyl, 6-amino-caproyl and derivatives thereof, wherein the carbon chain may be substituted or unsubstituted, saturated or unsaturated, hydroxylated or non-hydroxylated, sulfurated or non-sulfurated (SEQ ID NO: 5). More particularly, the invention concerns the said polypeptide wherein "n" is 0 and having the following structure A-Lys-X-Lys-B; A, X and B being defined herein (SEQ ID NO:6). In accordance with one particular aspect of the present invention, the polypeptide useful is a peptide of the sequence A-Lys-X-Lys-B wherein A may be —NH2, NH3+, or NH-D; D is an acyl group being biotin or an alkyl chain from 2 to 22 carbons, linear, or branched or cyclic, substituted or unsubstituted, saturated or unsaturated, hydroxylated or non-hydroxylated, sulfurated or non-sulfurated, wherein B may be H, O$^-$, OR1 or NR2R3 and R1, R2 and R3 independently either: a hydrogen atom, or an alkyl chain of from 1 to 24 carbons, linear, branched or cyclic, substituted or unsubstituted, saturated or unsaturated, hydroxylated or non-hydroxylated, sulfurated or non-sulfurated, and wherein X may be either a chain of two any amino acids (Xaa1Xaa2) which may be the same or different excluding arginine and lysine and excluding Xaa1Xaa2 being Thr-Thr, Gly-His and Glu-His (SEQ ID NO:6) or X is a spacer selected among the group comprising beta-alanyl, 5-amino-valeroyl, 4-amino-cyclohexanoyl, 4-amino-butyroyl, 6-amino-caproyl and derivatives thereof, whose the carbon chain may be substituted or unsubstituted, saturated or unsaturated, hydroxylated or non-hydroxylated, sulfurated or non-sulfurated.

It has been unexpectedly found that the polypeptides of the present invention can stimulate the production of certain advantageous biomolecules, such as, without limitation, collagen I, fibronectin and collagen IV in skin cells.

Another aspect of the present invention is cosmetic or dermopharmaceutical compositions including at least one of said polypeptides and a dermatologically acceptable carrier. It has now been discovered that the use of at least one polypeptide in accordance with the present invention in cosmetic, personal care or dermopharmaceutical compositions has anti-aging activity. Anti-aging activity means some degree or capacity for treating; preventing or ameliorating one or more signs, symptoms and/or causes of skin aging. For example, these polypeptides and compositions, which can enhance anti-aging effects and reduce signs of skin aging, can be used to treat or prevent wrinkles.

Methods of using these cosmetics and dermopharmaceuticals to improve the state and the appearance of human skin, and amongst others, to regulate visible and/or tactile discontinuities in skin associated, e.g. with skin aging, are also contemplated.

The present invention also is directed to the use of such compositions for the preparation of medicinal products useful for the treatment of signs of skin aging and in particular wrinkles, as well as for methods of their use in various cosmetic and dermatological applications.

DETAILED DESCRIPTION

All publications cited herein are hereby incorporated by reference in their entirety.

All percentages and ratios used herein are by weight of the total composition and all measurements made are at 25° C., unless otherwise designated.

Reference to a polypeptide in accordance with the present invention means a polypeptide corresponding to general formula (I):

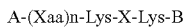

A-(Xaa)n-Lys-X-Lys-B wherein:
i) A=—NH2, NH3+, NH-D
D=an acyl group being biotin or an alkyl chain from 2 to 22 carbons, linear, or branched or cyclic, substituted or unsubstituted, saturated or unsaturated, hydroxylated or non-hydroxylated, sulfurated or non-sulfurated,
ii) B=H, O⁻, OR1 or NR2R3
and R1, R2 and R3 independently either: a hydrogen atom, or an alkyl chain of from 1 to 24 carbons, linear, branched or cyclic, substituted or unsubstituted, saturated or unsaturated, hydroxylated or non-hydroxylated, sulfurated or non-sulfurated,
iii) (Xaa)n is an amino acid chain and (Xaa) is any amino acid natural or non natural, excluding arginine and lysine,
iv) "n" is between 0 and 3
v) X being
either a chain of two any amino acids (Xaa1Xaa2), which may be the same or different excluding arginine and lysine, and excluding Xaa1Xaa2=Thr-Thr, Gly-His and Glu-His (SEQ ID NO: 4)
or a spacer selected among the group comprising beta-alanyl, 5-amino-valeroyl, 4-amino-cyclohexanoyl, 4-amino-butyroyl, 6-amino-caproyl and derivatives thereof, whose the carbon chain may be substituted or unsubstituted, saturated or unsaturated, hydroxylated or non-hydroxylated, sulfurated or non-sulfurated (SEQ ID NO: 5).

As used herein, "peptide" and "polypeptide" refer to both natural and synthetic peptides which can contain only natural amino acids, only non natural amino acids, or a combination of natural and non natural amino acids. As used herein, the term "polypeptide" includes oligopeptide, peptide, polypeptide and derivatives thereof, peptide analogs and derivatives thereof, as well as pharmaceutically acceptable salts of these compounds. "Peptide analog" means synthetically modified amino acids or peptide. As used herein, "peptides" encompass also complexes with other species such as metal ions (e.g., copper, zinc, manganese, magnesium, and the like).

The term "amino acid" as employed herein includes and encompasses all of the naturally occurring, and non natural amino acids, either in the D- or L-configuration if optically active. The term "non natural amino acids" encompasses synthetic amino acids and amino acids which are not considered as "natural amino acids".

The term "tripeptide" in accordance with the present invention is a compound that includes an uninterrupted sequence of three amino acids within its structure, and term "tetrapeptide" in accordance with the present invention is a compound that includes an uninterrupted sequence of four amino acids within its structure. These are indicated herein using a traditional three letter convention from left (N-terminal end) to right (C-terminal end). In this nomenclature, Gly is glycine, Ala is alanine, Thr is threonine, Phe is phenylalanine, Glu is glutamic acid, Gln is glutamine, Lys is lysine, Arg is arginine, Ava is 5-amino-valeric acid, βAla is beta-alanine, Abu is 4-amino-butyric-acid and Aca is 6-amino-caproic-acid.

In a particular embodiment of this invention, n=0 and the polypeptide is a peptide which can be represented by the following structure: A-Lys-X-Lys-B wherein A is —NH2, NH3+, NH-D, D is an acyl group being biotin or an alkyl chain from 2 to 22 carbons, linear, or branched or cyclic, substituted or unsubstituted, saturated or unsaturated, hydroxylated or non-hydroxylated, sulfurated or non-sulfurated, wherein B is H, O⁻, OR1 or NR2R3 and R1, R2 and R3 independently either: a hydrogen atom, or an alkyl chain of from 1 to 24 carbons, linear, branched or cyclic, substituted or unsubstituted, saturated or unsaturated, hydroxylated or non-hydroxylated, sulfurated or non-sulfurated, wherein X is either a chain of two any amino acids (Xaa1Xaa2), which may be the same or different excluding arginine and lysine and excluding Xaa1Xaa2=Thr-Thr, Gly-His and Glu-His (SEQ ID NO:6) or X is a spacer selected among the group comprising beta-alanyl, 5-amino-valeroyl, 4-amino-cyclohexanoyl, 4-amino-butyroyl, 6-amino-caproyl and derivatives thereof, whose the carbon chain may be substituted or unsubstituted, saturated or unsaturated, hydroxylated or non-hydroxylated, sulfurated or non-sulfurated.

In particularly preferred peptides, X is a chain of two amino acids (Xaa1Xaa2) in which Xaa1 is selected from the group comprising threonine, alanine and phenylalanine. In more preferred peptides, Xaa2 is an amino acid selected from the group comprising phenylalanine, alanine and tyrosine.

In another preferred embodiment, X is a spacer selected among the group comprising beta-alanyl, 5-amino-valeroyl, 4-amino-cyclohexanoyl, 4-amino-butyroyl, 6-amino-caproyl and derivatives thereof, wherein the carbon chain may be substituted or unsubstituted, saturated or unsaturated, hydroxylated or non-hydroxylated, sulfurated or non-sulfurated. In more preferred embodiment X is selected among the group comprising beta-alanyl, 5-amino-valeroyl, 4-amino-cyclohexanoyl, 4-amino-butyroyl, and 6-amino-caproyl.

In order to enhance the bioavailability and cutaneous barrier crossing of those peptides, their lipophilicity or lipophilic character can be increased either by acylation of the N-terminal NH2 group of the peptide, by esterification of the carboxyl group with an alcohol, linear or branched, saturated or unsaturated, hydroxylated or not, or both.

In another preferred embodiment, the said acyl group is bound to the N-terminal end of at least one amino acid and is a straight-chain or branched-chain, long or short chain, saturated or unsaturated, substituted with one or more hydroxyl, amino, acyl amino, sulfate or sulfide groups or may be unsubstituted, and which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid, biotinic acid, folic acid, decanoic acid, retinoic acid, sorbic acid, caproic acid, undecanoic acid, nicotinic acid, azelaic acid, propionic acid, butyric acid, valeric acid, lactic acid, malic acid or mixtures thereof.

In preferred methods of implementation of the invention, N-acyl groups used are lauroyl ($C_{12}$) or myristoyl ($C_{14}$) or palmitoyl ($C_{16}$) or stearoyl ($C_{18}$) or oleoyl ($C_{18:1}$) or arachidic ($C_{20}$) or linoleoyl ($C_{18:2}$) or lipoyl or biotinyl (also called biotinoyl) or oleoyl or acetyl or elaidoyl or aleoyl or octanoyl. In a particularly preferred embodiment the N terminal group is H, Elaidoyl or Palmitoyl.

Peptides and derivatives in accordance with the present invention include, without limitation, Pal-Lys-Thr-Phe-Lys (SEQ ID NO: 7), Ela-Lys-Thr-Phe-Lys (SEQ ID NO: 8), Ela-Lys-Thr-Ala-Lys (SEQ ID NO: 9), Pal-Lys-Ava-Lys, Ela-Lys-Ala-Tyr-Lys (SEQ ID NO: 10), Ela-Lys-Phe-Tyr-Lys (SEQ ID NO: 11), Pal-Lys-βAla-Lys, Pal-Lys-Abu-Lys and Pal-Lys-Aca-Lys. "N-Pal" or "Pal" refers to an N-palmitoyl derivative. Likewise, "N-Ela" or "Ela" refers to an N-elaidoyl derivative.

The polypeptides of the present invention can be obtained by chemical or enzymatic synthesis from the constitutive amino acids or of their derivatives; or is obtained by mild hydrolysis of natural proteins; or by biotechnology. For example, for the synthesis of the polypeptides of the invention, known peptide chemistry methods and particularly the Fmoc/tBu solid phase method may be used. Other chemistry may also be used such as Boc/bzl or liquid phase chemistry.

In a particular embodiment, the polypeptides of the present invention form together with acids mono- or polyvalent, homogeneous or mixed salts, preferably with inorganic acids, or with appropriate organic aliphatic saturated or unsaturated carboxylic acids, or with aromatic carboxylic acids, or with aromatic-aliphatic carboxylic acids, or with heteroaromatic carboxylic acids, or with aliphatic or aromatic sulfonic acids, preferably with acetic acid, lactic acid and/or chlorhydric acid.

The amino acids mentioned in formula (I) can have an L or D configuration, or represent a mixture of both configurations. The compounds are present as isomeric forms and mixture thereof, and as mixtures of rotamers.

The present invention relates also to a cosmetic or dermopharmaceutical composition comprising a safe and effective amount of at least one compound of the general formula (I) (SEQ ID NO: 4 and SEQ ID NO:5) defined herein and a dermatologically acceptable carrier.

In one preferred aspect of the present invention, there is provided compositions which comprise at least one compound of the general formula (I) (SEQ ID NO:4 and SEQ ID NO:5) defined herein which have anti-aging activity in an amount which is effective to treat at least one signs of aging, and a dermatologically acceptable carrier.

While the specification concludes with the claims particularly pointing and distinctly claiming the invention, it is believed that the present invention will be better understood from the following description. The terms "having" and "including" are to be construed as open-ended unless the context suggests otherwise.

The compositions of the present invention can comprise or consist essentially of the components of the present invention as well as other ingredients described herein. As used herein, "consisting essentially of" means that the composition or component may include additional ingredients, but only if the additional ingredients do not materially alter the basic and novel characteristics of the claimed compositions or methods. Preferably, such additives will not be present at all or only in trace amounts.

The term "dermatologically acceptable", as used herein, means that the compositions or components described are suitable for use in contact with human skin without risk of toxicity, incompatibility, instability, allergic response, and the like.

All terms such as "skin aging", "signs of skin aging", "topical application", and the like are used in the sense in which they are generally and widely used in the art of developing, testing and marketing cosmetic and personal care products. The term "cosmetic composition" or more briefly just "composition" in accordance with the present invention relates to a formulation that can be used for cosmetic purposes, purposes of hygiene or as a basis for delivery of one or more dermopharmaceutical ingredients. This includes cosmetics, personal care products and pharmaceutical preparations. It is also possible that these formulations are used for two or more of these same purposes at one time. A medicated dandruff shampoo, for example, has pharmacological properties and is used as a personal care product to provide clean hair.

"Signs of skin aging" and other phrases similarly referring to, for example, symptoms of aging and the like include, but are not limited to, all outward visibly and tactilely perceptible manifestations as well as any other macro or micro effects due to skin aging. Such signs may be induced or caused by intrinsic factors and/or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown and other histological changes in the stratum corneum, dermis, epidermis, the skin vascular system (e.g., telangiectasia or spider vessels), and underlying tissues, especially those proximate to the skin. As used herein, the term "visible and/or tactile discontinuities in skin" may encompass the stretch marks. Particularly preferred in accordance with the present invention, the signs of skin aging are wrinkles and the compositions of the present invention are, in certain preferred embodiments, useful in fighting, treating (prophylactically and/or therapeutically) or preventing wrinkles. In the context of the present invention "wrinkles" means wrinkles associated with intrinsic factors and/or extrinsic factors induced skin aging (such as e.g., advancing age, or sun-induced or pollution-induced skin aging).

As used herein, treating by prophylactically regulating a skin condition includes delaying, minimizing and/or preventing visible and/or tactile discontinuities in skin (e.g., texture irregularities in the skin which may be detected visually or by feel), including signs of skin aging.

As used herein, treating by therapeutically regulating skin condition includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition.

Some of the products and compositions of the present invention are useful for improving skin appearance and/or feel of skin exhibiting signs of skin aging. For example, preferred compositions of the present invention are useful for regulating the appearance of skin conditions by providing a visual improvement in skin appearance following application of the composition to the skin such as a reduction in the apparent width or depth or length of wrinkles to an observer.

Some of the compositions of the present invention may also provide additional benefits, including stability, absence of significant (consumer-unacceptable) skin irritation, anti-inflammatory activity and good aesthetics.

In certain preferred aspects, the present invention is useful for improving the physiological state and/or the physical appearance of human skin, in particular to reduce the signs of skin aging that are generated by sun exposure, physical and hormonal stress, abrasion, nutritional effects and other similar causes. The compositions may often be used to prevent the signs of aging and/or to treat them in order to afford the consumer who uses them, a more youthful appearance.

In a particularly preferred embodiment, the composition of the present invention contains at least one compound of the general formula (I) defined herein where "n"=0 and thus where said compound has the following structure: A-Lys-X-Lys-B wherein A=—NH2, NH3+, NH-D, D is an acyl group being biotin or an alkyl chain from 2 to 22 carbons, linear, or branched or cyclic, substituted or unsubstituted, saturated or unsaturated, hydroxylated or non-hydroxylated, sulfurated or non-sulfurated, wherein B=H, O−, OR1 or NR2R3 and R1, R2 and R3 independently either: a hydrogen atom, or an alkyl chain of from 1 to 24 carbons, linear, branched or cyclic, substituted or unsubstituted, saturated or unsaturated, hydroxylated or non-hydroxylated, sulfurated or non-sulfurated, wherein X is either a chain of two any amino acids (Xaa1Xaa2), which may be the same or different excluding arginine, lysine and excluding Xaa1Xaa2=Thr-Thr, Gly-His and Glu-His (SEQ ID NO:6) or X is a spacer selected among the group comprising beta-alanyl, 5-amino-valeroyl, 4-amino-cyclohexanoyl, 4-amino-butyroyl, 6-amino-caproyl and derivatives thereof, wherein the carbon chain may be substituted or unsubstituted, saturated or unsaturated, hydroxylated or non-hydroxylated, sulfurated or non-sulfurated; and a dermatologically acceptable carrier.

In preferred embodiments, the cosmetic or dermopharmaceutical compositions according to the invention contain at least one compound of the general formula (I) defined herein and a dermatologically acceptable carrier, wherein X is a chain of two amino acid (Xaa1Xaa2) (SEQ ID NO:4 or SEQ ID NO:6) wherein Xaa1 is selected from the group comprising threonine, alanine and phenylalanine. In more preferred embodiments, Xaa2 is an amino acid selected from the group comprising phenylalanine, alanine and tyrosine.

In another preferred embodiment, the cosmetic or dermopharmaceutical composition according to the invention contains at least one compound of the general formula (I) (SEQ ID NO: 5) defined herein and a dermatologically acceptable carrier, wherein X is a spacer selected among the group comprising beta-alanyl, 5-amino-valeroyl, 4-amino-cyclohexanoyl, 4-amino-butyroyl, 6-amino-caproyl and derivatives thereof. In more preferred embodiment X is selected among the group comprising beta-alanyl, 5-amino-valeroyl, 4-amino-cyclohexanoyl, 4-amino-butyroyl, and 6-amino-caproyl.

In a particularly preferred embodiment, the cosmetic or dermopharmaceutical composition according to the invention contains at least Palmitoyl-Lys-Thr-Phe-Lys (SEQ ID NO: 7), or at least Ela-Lys-Thr-Phe-Lys (SEQ ID NO: 8), or at least Ela-Lys-Thr-Ala-Lys (SEQ ID NO: 9), or at least Palmitoyl-Lys-Ava-Lys, or at least Ela-Lys-Ala-Tyr-Lys (SEQ ID NO: 10) or at least Ela-Lys-Phe-Tyr-Lys (SEQ ID NO: 11), or at least Pal-Lys-βAla-Lys, or at least Pal-Lys-Abu-Lys or at least Pal-Lys-Aca-Lys.

Polypeptides are used in cosmetic and dermopharmaceutical compositions as per the invention at concentration which may range from 0.00001% (w/w) to 15% (w/w) preferably between 0.0001% (w/w) to 0.1% (w/w) by weight of the composition.

In a particular embodiment, the composition of the present invention contains further one or more skin anti-aging agent, or anti-wrinkle agent, or anti-atrophy agent or anti-oxidant/radical scavenger.

I. ADDITIVES

According to the invention, the dermatologically acceptable carrier can be an aqueous or hydroalcoholic solution, a water in oil emulsion, an oil in water emulsion, a microemulsion, an aqueous gel, an anhydrous gel, a serum or a vesicle dispersion.

The compositions of the invention may include various other and additional ingredients, which may be active, functional, conventionally used in cosmetic, personal care or topical/transdermal pharmaceutical products or otherwise. Of course, a decision to include an additional ingredient and the choice of specific additional ingredients depends on the specific application and product formulation. Also, the line of demarcation between an "active" ingredient and an "inactive" ingredient" is artificial and dependent on the specific application and product type. A substance that is an "active" ingredient in one application or product may be a "functional" ingredient in another, and vice versa.

Thus, the compositions of the invention may include at least one skin care active. As used herein, "skin care actives" are additional ingredients, which provide some benefit to the object of the composition. Such additional ingredients may include one or more substances such as, without limitations, cleaning agents, hair conditioning agents, skin conditioning agents, hair styling agents, antidandruff agents, hair growth promoters, perfumes, sunscreen and/or sunblock compounds, pigments, moisturizers, film formers, hair colors, make-up agents, detergents, pharmaceuticals, thickening agents, emulsifiers, humectants, emollients, antiseptic agents, deodorant actives, dermatologically acceptable carriers and surfactants.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

In a preferred embodiment, where the composition is to be in contact with human keratinous tissue, the additional ingredients should be suitable for application to keratinous tissue, that is, when incorporated into the composition they are suitable for use in contact with human keratinous tissue (hair, nails, skin, lips) without undue toxicity, incompatibility, instability, allergic response, and the like within the scope of sound medical judgment.

The CTFA Cosmetic Ingredient Handbook, Tenth Edition (published by the Cosmetic, Toiletry, and Fragrance Association, Inc., Washington, D.C.) (2004) describes a wide variety of nonlimiting materials that can be added to the composition herein. Examples of actives which may be added, include, but are not limited to: skin soothing and healing agents, skin anti-aging agents, skin moisturizing agents, anti-wrinkle agents, anti-atrophy agents, skin smoothing agents, antibacterial agents, antifungal agents, pesticides, anti parasitic agents, antimicrobial agents, anti-inflammatory agents, anti-pruriginous agents, external anaesthetic agents, antiviral agents, keratolytic agents, free radicals scavengers, antiseborrheic agents, antidandruff agents, the agents modulating the differentiation, proliferation or pigmentation of the skin and agents accelerating penetration, desquamating agents, depigmenting or propigmenting agents, antiglycation agents, tightening agents, agents stimulating the synthesis of dermal or epidermal macromolecules and/or preventing their degradation; agents stimulating the proliferation of fibroblasts and/or keratinocytes or stimulating the differentiation of keratinocytes; muscle relaxants; antipollution and/or anti-free radical agents; slimming agents, anticellulite agents, agents acting on the microcirculation; agents acting on the energy metabolism of the cells; cleaning agents, hair conditioning agents, hair styling agents, hair growth promoters, sunscreen and/or sunblock compounds, make-up agents, detergents, pharmaceutical drugs, emulsifiers, emollients, antiseptic agents, deodorant actives, dermatologically acceptable carriers, surfactants, abrasives, absorbents, aesthetic components such as fragrances, colorings/colorants, essential oils, skin sensates, cosmetic astringents, anti-acne agents, anti-caking agents, anti foaming agents, antioxidants, binders, biological additives, enzymes, enzymatic inhibitors, enzyme-inducing agents, coenzymes, plant extracts, plant derivatives, plant tissue extracts, plant seed extracts, plant oils, botanicals, botanical extracts, ceramides, peptides, buffering agents, bulking agents, chelating agents, chemical additives, colorants, cosmetic biocides, denaturants, drug astringents, external analgesics, film formers or materials, e.g., polymers, for aiding the film-forming properties and substantivity of the composition, quaternary derivatives, agents increasing the substantivity, opacifying agents, pH adjusters, pH regulator (e.g. triethanolamine), propellants, reducing agents, sequestrants, skin bleaching and lightening agents, skin tanning agents, skin-conditioning agents (e.g., humectants, including miscellaneous and occlusive), skin soothing and/or healing agents and derivatives, skin treating agents, thickeners, lipid thickener (e.g. stearic acid), vitamins and derivatives thereof, peeling agents, moisturizing agents, curative agents, lignans, preservatives (e.g. phoxyethanol and parabens), UV absorbers, a cytotoxic, an anti-neoplastic agent, a fat-soluble active, suspending agents, viscosity modifiers, dyes, non-volatile solvents, diluents, pearlescent aids, foam boosters, a vaccine, a water-soluble sunscreen, antiperspirant, depilatory, perfumed water, fat soluble sunscreens substance intended to improve the state of dry or aged skin, skin restructuring agent (e.g. *Siegesbeckia orientalis* extract), emollient (e.g. C12-15 alkyl benzoate), excipients, fillers, minerals, anti-mycobacterial agents, anti-allergenic agents, H1 or H2 antihistamines, anti-irritants, immune system boosting agents, immune system suppressing agents, insect repellents, lubricants, staining agents, hypopigmenting agents, preservatives, photostabilizing agents and their mixture.

Said additional ingredient is selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, peptides and their derivatives, di-, tri-, tetra-, penta-, and hexapeptides and their derivatives, Lys-Thr-Thr-Lys-Ser (SEQ ID NO: 1), palmitoyl-Lys-Thr-Thr-Lys-Ser (SEQ ID NO:2), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins their salts and derivatives, provitamins and their salts and derivatives, ethyl panthenol, vitamin B, vitamin B derivatives, vitamin B1, vitamin B2, vitamin B6, vitamin B12, vitamin K, vitamin K derivatives, pantothenic acid and its derivatives, pantothenyl ethyl ether, panthenol and its derivatives, dexpanthenol, ethyl panthenol, biotin, amino acids and their salts and derivatives, water soluble amino acids, asparagine, alanine, indole, glutamic acid, water insoluble vitamins, vitamin A, vitamin E, vitamin F, vitamin D, mono-, di-, and tri-terpenoids, beta-ionol, cedrol, and their derivatives, water insoluble amino acids, tyrosine, tryptamine, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove oil, menthol, camphor, eucalyptus oil, eugenol, menthyl lactate, witch hazel distillate, eicosene and vinyl pyrrolidone copolymers, iodopropyl butylcarbamate, a polysaccharide, an essential fatty acid, salicylate, glycyrrhetinic acid, carotenoides, ceramides and pseudo-ceramides, a lipid complex, oils in general of natural origin such Shea butter, apricot oil, onagre oil, prunus oil, palm oil, monoi oil, HEPES; procysteine; O-octanoyl-6-D-maltose; the disodium salt of methylglycinediacetic acid, steroids such as diosgenin and derivatives of DHEA; N-ethyloxycarbonyl-4-para-aminophenol, bilberry extracts; phytohormones; extracts of the yeast *Saccharomyces cerevisiae*; extracts of algae; extracts of soybean, lupin, maize and/or pea; alverine and its salts, in particular alverine citrate, extract of butcher's broom and of horse chestnut, and mixtures thereof, without this list being limiting. Further skin care and hair care active ingredients that are particularly useful in combination with the polypeptides can be found in SEDERMA commercial literature and on the website www.sederma.fr (herewith incorporated in its entirety).

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

1. Sugar Amines (Amino Sugars)

The compositions of the present invention can comprise a sugar amine, which is also known as amino sugar. Sugar amine compounds useful in the present invention can include those described in PCT Publication WO 02/076423 and U.S. Pat. No. 6,159,485.

In one embodiment, the composition comprises from about 0.01% to about 15%, more preferably from about 0.1% to about 10%, and even more preferably from about 0.5% to about 5% by weight of the composition, of sugar amine.

Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, "sugar amine" includes isomers and tautomers of such and its salts (e.g., HCl salt) and is commercially available from Sigma Chemical Co.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt).

Preferred for use herein are glucosamine, particularly D-glucosamine and N-acetyl glucosamine, particularly N-acetyl-D-glucosamine.

2. Vitamin B3 Compounds

The compositions of the present invention can include a vitamin B3 compound. Vitamin B3 compounds are particularly useful for regulating skin conditions, as described in U.S. Pat. No. 5,939,082. In one embodiment, the composition comprises from about 0.001% to about 50%, more preferably from about 0.01% to about 20%, even more preferably from about 0.05% to about 10%, and still more preferably from about 0.1% to about 7%, even more preferably from about 0.5% to about 5%, by weight of the composition, of the vitamin B3 compound.

As used herein, "vitamin B3 compound" means a compound having the formula:

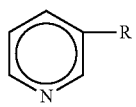

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g, tocopherol nicotinate, myristyl nicotinate), nicotinyl amino acids, nicotinyl alcohol esters of carboxylic acids, nicotinic acid N-oxide and niacinamide N-oxide.

Suitable esters of nicotinic acid include nicotinic acid esters of C1-C22, preferably C1-C16, more preferably C1-C6 alcohols. Non-vasodilating esters of nicotinic acid include tocopherol nicotinate and inositol hexanicotinate; tocopherol nicotinate is preferred.

Other derivatives of the vitamin B3 compound are derivatives of niacinamide resulting from substitution of one or more hydrogens of the amide group. Specific examples of such derivatives include nicotinuric acid ($C_8H_8N_2O_3$) and nicotinyl hydroxamic acid ($C_6H_6N_2O_2$).

Exemplary nicotinyl alcohol esters include nicotinyl alcohol esters of the carboxylic acids salicylic acid, acetic acid, glycolic acid, palmitic acid and the like. Other non-limiting examples of vitamin B3 compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl)urea, 2-mercaptonicotinic acid, nicomol, and niaprazine.

Examples of the above vitamin B3 compounds are well known in the art and are commercially available from a number of sources, e.g., the Sigma Chemical Company; ICN Biomedicals, Inc. and Aldrich Chemical Company.

One or more vitamin B3 compounds may be used herein. Preferred vitamin B3 compounds are niacinamide and tocopherol nicotinate. Niacinamide is more preferred.

When used, salts, derivatives, and salt derivatives of niacinamide are preferably those having substantially the same efficacy as niacinamide.

Salts of the vitamin B3 compound are also useful herein. Nonlimiting examples of salts of the vitamin B3 compound useful herein include organic or inorganic salts, such as inorganic salts with anionic inorganic species (e.g., chloride, bromide, iodide, carbonate, preferably chloride), and organic carboxylic acid salts (including mono-, di- and tri-C1-C18 carboxylic acid salts, e.g., acetate, salicylate, glycolate, lactate, malate, citrate, preferably monocarboxylic acid salts such as acetate). These and other salts of the vitamin B3 compound can be readily prepared by the skilled artisan (<<The Reaction of L-Ascorbic and D-Iosascorbic Acid with Nicotinic Acid and Its Amide", J. Organic Chemistry, Vol. 14, 22-26 (1949)).

The vitamin B3 compound may be included as the substantially pure material, or as an extract obtained by suitable physical and/or chemical isolation from natural (e.g., plant) sources. The vitamin B3 compound is preferably substantially pure, more preferably essentially pure.

3. Dehydroacetic Acid (DHA)

The composition of this invention can include dehydroacetic acid, having the structure:

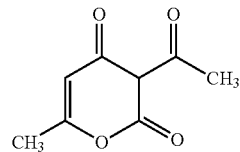

or pharmaceutically acceptable salts, derivatives or tautomers thereof. The technical name for dehydroacetic acid is 3-Acetyl-6-methyl-2H-pyran-2,4(3H)-dione and can be commercially purchased from Lonza.

Pharmaceutically acceptable salts include alkali metal salts, such as sodium and potassium; alkaline earth metal salts, such as calcium and magnesium; non-toxic heavy metal salts; ammonium salts; and trialkylammonium salts, such astrimethylammonium and triethylammonium. Sodium, potassium, and ammonium salts of dehydroacetic acid are preferred. Highly preferred is sodium dehydroacetate which can be purchased from Tri-K, as Tristat SDHA. Derivatives of dehydroacetic acid include, but are not limited to, any compounds wherein the $CH_3$ groups are individually or in combination replaced by amides, esters, amino groups, alkyls, and alcohol esters. Tautomers of dehydroacetic acid can be described as having the chemical formula $C_8H_8O_4$ and generally having the structure above.

In one embodiment, the compositions of the present invention can comprise from about 0.001% to about 25% by weight of the composition, preferably from about 0.01% to about 10%, more preferably from about 0.05% to about 5%, and even more preferably from about 0.1% to about 1%, of dehydroacetic acid or pharmaceutically acceptable salts, derivatives or tautomers thereof.

4. Phytosterol

The compositions of the present invention can comprise a phytosterol. For example, one or more phytosterols can be selected from the group consisting of β-sitosterol, campesterol, brassicasterol, Δ5-avennasterol, lupenol, α-spinasterol, stigmasterol, their derivatives, analogs, and combinations thereof. More preferably, the phytosterol is selected from the group consisting of β-sitosterol, campesterol, brassicasterol, stigmasterol, their derivatives, and combinations thereof. More preferably, the phytosterol is stigmasterol.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company, Sigma Chemical Company and Cognis.

In one embodiment, the composition of the present invention comprises from about 0.0001% to about 25%, more preferably from about 0.001% to about 15%, even more preferably from about 0.01% to about 10%, still more preferably from about 0.1% to about 5%, and even more preferably from about 0.2% to about 2% of phytosterol, by weight of the composition.

5. Salicylic Acid Compound

The compositions of the present invention may comprise a salicylic acid compound, its esters, its salts, or combinations thereof. In one embodiment of the compositions of the present invention, the composition preferably comprises from about 0.0001% to about 25%, more preferably from about 0.001% to about 15%, even more preferably from about 0.01% to about 10%, still more preferably from about 0.1% to about 5%, and even more preferably from about 0.2% to about 2%, by weight of the composition, of salicylic acid compound.

6. Hexamidine

The compositions of the present invention can include hexamidine compounds, its salts, and derivatives.

In one embodiment, the composition comprises from about 0.0001% to about 25%, more preferably from about 0.001% to about 10%, more preferably from about 0.01% to about 5%, and even more preferably from about 0.02% to about 2.5% of hexamidine by weight of the composition.

As used herein, hexamidine derivatives include any isomers and tautomers of hexamidine compounds including but not limited to organic acids and mineral acids, for example sulfonic acid, carboxylic acid, etc. Preferably, the hexamidine compounds include hexamidine diisethionate, commercially available as Eleastab® HP100 from Laboratoires Serobiologiques.

7. Dialkanoyl Hydroxyproline Compounds

The compositions of the present invention can comprise one or more dialkanoyl hydroxyproline compounds and their salts and derivatives.

In one embodiment, the dialkanoyl hydroxyproline compounds are preferably added to the composition from about 0.01% to about 10%, more preferably from about 0.1% to about 5%, even more preferably from about 0.1% to about 2% by weight of the composition Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalmitoyl hydroxyproline includes any isomers and tautomers of such and is commercially available under the tradename Sepilift DPHP® from Seppic, Inc. Further discussion of dipalmitoyl hydroxyproline appears in PCT Publication WO 93/23028. Preferably, the dipalmitoyl hydroxyproline is the triethanolamine salt of dipalmitoyl hydroxyproline.

8. Flavonoids

The compositions of the present invention can comprise a flavonoid compound. Flavonoids are broadly disclosed in U.S. Pat. Nos. 5,686,082 and 5,686,367. As used herein, "flavonoid" means unsubstituted flavonoid or substituted flavonoid (i.e. mono-substituted flavonoid, or/and di-substituted flavonoid, or/and tri-substituted flavonoid). Examples of flavonoids particularly suitable for use in the present invention are one or more flavones, one or more flavanones, one or more isoflavones, one or more coumarins, one or more chromones, one or more dicoumarols, one or more chromanones, one or more chromanols, isomers (e.g., cis/trans isomers) thereof, and mixtures thereof.

Preferred for use herein are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy) and other plant sources of such mixtures (e.g., red clover), and mixtures thereof. Also preferred are favanones such as hesperitin, hesperidin, and mixtures thereof.

Flavonoid compounds useful herein are commercially available from a number of sources, e.g., Indofine Chemical Company, Inc., Steraloids, Inc., and Aldrich Chemical Company, Inc. Suitable flavonoids are commercially available called Sterocare® offered by SEDERMA and described in WO 99/18927.

In one embodiment, the herein described flavonoid compounds may be added from about 0.01% to about 20%, more preferably from about 0.1% to about 10%, and even more preferably from about 0.5% to about 5%, by weight of the composition.

9. N-Acyl Amino Acid Compound

The topical compositions of the present invention can comprise one or more N-acyl amino acid compounds. The amino acid can be one of any of the amino acids known in the art. The N-acyl amino acid compounds of the present invention can correspond to the formula:

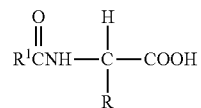

wherein R can be a hydrogen, alkyl (substituted or unsubstituted, branched or straight chain), or a combination of alkyl and aromatic groups.

Preferably, the N-acyl amino acid compound is selected from the group comprising N-acyl Phenylalanine, N-acyl Tyrosine, their isomers, their salts, and derivatives thereof. The amino acid can be the D or L isomer or a mixture thereof.

Among the broad class of N-acyl Phenylalanine derivatives, particularly useful is N-undecylenoyl-L-phenylalanine commercially available under the tradename Sepiwhite® from SEPPIC.

In one embodiment, the present invention preferably comprises from about 0.0001% to about 25%, more preferably from about 0.001% to about 10%, more preferably from about 0.01% to about 5%, and even more preferably from about 0.02% to about 2.5% of the N-acyl amino acid by weight of the composition.

10. Retinoid

The compositions of this invention can comprise a retinoid, preferably in a safe and effective amount such that the resultant composition is safe and effective for regulating keratinous tissue condition, preferably for regulating visible and/or tactile discontinuities in keratinous tissue (e.g., regulating signs of skin aging). The compositions can comprise from about 0.001% to about 10%, more preferably from about 0.005% to about 2%, even more preferably from about 0.01% to about 1%, still more preferably from about 0.01% to about 0.5%, by weight of the composition, of the retinoid. The optimum concentration used in a composition will depend on the specific retinoid selected since their potency can vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably selected from retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), or mixtures thereof. More preferably the retinoid is a retinoid other than retinoic acid. These compounds are well known in the art and are commercially available from a number of sources, e.g., Sigma Chemical Company, and Boerhinger Mannheim. Other retinoids which are useful herein are described in U.S. Pat. Nos. 4,677,120, U.S. Pat. No. 4,885,311, U.S. Pat. No. 5,049,584, U.S. Pat. No. 5,124,356, and Reissue 34,075. Other suitable retinoids can include tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids include retinol, retinyl palmitate, retinyl acetate, retinyl propionate, retinal and combinations thereof. More preferred is retinyl propionate, used most preferably from about 0.1% to about 0.3%.

The retinoid may be included as the substantially pure material, or as an extract obtained by suitable physical and/or chemical isolation from natural (e.g., plant) sources. The retinoid is preferably substantially pure, more preferably essentially pure.

11. Optional Peptide

The composition of the present invention can comprise an additional peptide. Suitable peptides can include, but are not limited to, di-, tri-, tetra-, penta-, and hexa-peptides and derivatives thereof. In one embodiment, the composition comprises from about $1\times10^{-7}$% to about 20%, more preferably from about $1\times10^{-6}$% to about 10%, even more preferably from about $1\times10^{-5}$% to about 5%, by weight of additional peptide.

As used herein, "additional peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides.

Suitable additional dipeptides for use herein include but are not limited to Carnosine (beta-Ala-His), Tyr-Arg, Val-Trp (WO 0164178), Asn-Phe, Asp-Phe. Suitable additional tripeptides for use herein include, but are not limited to Arg-Lys-Arg (Peptide CK), His-Gly-Gly, Gly-His-Lys, Gly-Gly-His, Gly-His-Gly, Lys-Phe-Lys. Suitable additional tetrapeptides for use herein include but are not limited to, Arg-Ser-Arg-Lys (SEQ ID NO: 12) and Gly-Gln-Pro-Arg (SEQ ID NO: 13). Suitable additional pentapeptides include, but are not limited to Lys-Thr-Thr-Lys-Ser (SEQ ID NO: 1). Suitable hexapeptides include but are not limited to Val-Gly-Val-Ala-Pro-Gly (SEQ ID NO: 14) and such as those disclosed in Fr 2854897 and US 2004/0120918.

Other suitable additional peptides for use herein include, but are not limited to lipophilic derivatives of peptides, preferably palmitoyl derivatives, and metal complexes of the aforementioned (e.g., copper complex of the tripeptide His-Gly-Gly). Preferred additional dipeptide derivatives include N-Palmitoyl-beta-Ala-His, N-Acetyl-Tyr-Arg-hexadecylester (CALMOSENSINE™ from SEDERMA, France, WO 9807744, U.S. Pat. No. 6,372,717). Preferred additional tripeptide derivatives include N-Palmitoyl-Gly-Lys-His, (Pal-GKH from SEDERMA, France, WO 0040611), a copper derivative of His-Gly-Gly sold commercially as lamin, from Sigma, lipospondin (N-Elaidoyl-Lys-Phe-Lys) and its analogs of conservative substitution, N-Acetyl-Arg-Lys-Arg-NH2 (Peptide CK+), N-Biot-Gly-His-Lys (N-Biot-GHK from SEDERMA, WO 0058347) and derivatives thereof. Suitable additional tetrapeptide derivatives for use herein include, but are not limited to N-palmitoyl-Gly-Gln-Pro-Arg (SEQ ID NO: 15, from SEDERMA, France), suitable additional pentapeptide derivatives for use herein include, but are not limited to N-Palmitoyl-Lys-Thr-Thr-Lys-Ser (SEQ ID NO: 2, available as MATRIXYL™ from SEDERMA, France, WO 0015188 and U.S. Pat. No. 6,620,419), N-Palmitoyl-Tyr-Gly-Gly-Phe-X (SEQ ID NO: 16) with X Met or Leu or mixtures thereof. Suitable additional hexapeptide derivatives for use herein include, but are not limited to N-Palmitoyl-Val-Gly-Val-Ala-Pro-Gly (SEQ ID NO: 3) and derivatives thereof.

The preferred compositions commercially available containing a additional tripeptide or a derivative include Biopeptide-CL™ by SEDERMA (WO 0143701), Maxilip™ by SEDERMA (WO 0143701), Biobustyl™ by SEDERMA. The compositions commercially available preferred sources of additional tetrapeptides include RIGIN™ (WO 0043417), EYELISS™ (WO 03068141), MATRIXYL™, and MATRIXYL3000™ which contain between 50 and 500 ppm of palmitoyl-Gly-Gln-Pro-Arg (SEQ ID NO: 15), and carrier, proposed by SEDERMA, France (US 2004/0132667).

12. Ascorbates and Other Vitamins

The compositions of the present invention may comprise one or more vitamins, such as ascorbates (e.g., vitamin C, vitamin C derivatives, ascorbic acid, ascorbyl glucoside, ascorbyl palmitate, magnesium ascorbyl phosphate, sodium ascorbyl phosphate). Such vitamins can include, but are not limited to, vitamin B, vitamin B derivatives, vitamin B1 to vitamin B12 and theirs derivatives, vitamin K, vitamin K derivatives, vitamin H vitamin D, vitamin D derivatives, vitamin E, vitamin E derivatives, and provitamins thereof, such as panthenol and mixtures thereof. The vitamin compounds may be included as the substantially pure material, or as an extract obtained by suitable physical and/or chemical isolation from natural (e.g., plant) sources. In one embodiment, when vitamin compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the vitamin compound.

13. Particulate Material

The compositions of the present invention can comprise one or more particulate materials. Non limiting examples of particulate materials useful in the present invention include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged, and can be added to the current compositions as a powder or as a pre-dispersion. In one embodiment, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition.

Particulate materials useful herein can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, aluminum oxide, silicone resin, barium sulfate, calcium carbonate, cellulose acetate, PTFE, polymethyl methacrylate, starch, modified starches such as aluminun starch octenyl succinate, silk, glass, and mixtures thereof. Preferred organic powders/fillers include, but are not limited, to polymeric particles chosen from the methylsilsesquioxane resin microspheres such as, for example, those sold by Toshiba silicone under the name Tospearl 145A, microspheres of polymethylmethacrylates such as those sold by Seppic under the name Micropearl M 100, the spherical particles of crosslinked polydimethylsiloxanes, especially such as those sold by Dow Corning Toray Silicone under the name Trefil E 506C or Trefil E 505C, spherical particles of polyamide and more specifically Nylon 12, especially such as those sold by Atochem under the name Orgasol 2002D Nat C05, polystyrene microspheres such as for example those sold by Dyno Particles under the name Dynospheres, ethylene acrylate copolymer sold by Kobo under the name FloBead EA209, PTFE, polypropylene, aluminium starch octenylsuccinate such as those sold by National Starch under the name Dry Ho, microspheres of polyethylene such as those sold by Equistar under the name of Microthene FN510-00, silicone resin, polymethylsilsesquioxane silicone polymer, platelet shaped powder made from L-lauroyl lysine, and mixtures thereof.

Also useful herein are interference pigments. The most common examples of interference pigments are micas layered with about 50-300 nm films of TiO2, Fe2O3, silica, tin oxide, and/or Cr2O3. Useful interference pigments are available commercially from a wide variety of suppliers, for example, Rona (Timiron™ and Dichrona™), Presperse (Flonac™), Englehard (Duochrome™), Kobo (SK-45-R and SK-45-G), BASF (Sicopearls) and Eckart (e.g. Prestige Silk Red).

Other pigments useful in the present invention can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or ZrO2, are commercially available from a number of sources. One example of a suitable particulate material contains the material available from U.S. Cosmetics (TRONOX TiO2 series, SAT-T CR837, a rutile TiO2).

The pigments/powders of the current invention can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobic treatments being preferred.

14. Sunscreen Actives

The compositions of the subject invention may optionally contain a sunscreen active. As used herein, "sunscreen active" includes both sunscreen agents and physical sunblocks. Suitable sunscreen actives may be organic or inorganic.

A wide variety of conventional organic or inorganic sunscreen actives are suitable for use herein. In one embodiment, the composition comprises from about 0.1% to about 20%, more typically from about 0.5% to about 10% by weight of the composition, of the sun screen active. Exact amounts will vary depending upon the sunscreen chosen and the desired Sun Protection Factor (SPF).

As examples of organic screening agents which are active in UV-A and/or UV-B, there may be mentioned in particular those designated below by their CTFA name:

para-aminobenzoic acid derivatives: PABA, Ethyl PABA, Ethyl Dihydroxypropyl PABA, Ethylhexyl Dimethyl PABA sold in particular under the name "ESCALOL 507" by ISP, Glyceryl PABA, PEG-25 PABA sold under the name "UVINUL P25" by BASF, salicyclic derivatives: Homosalate sold under the name "EUSOLEX HMS" by RONA/EM INDUSTRIES, Ethylhexyl Salicylate sold under the name "NEO HELIOPAN OS" by HAARMANN and REIMER, Dipropyleneglycol Salicylate sold under the name "DIPSAL" by SCHER, TEA Salicylate, sold under the name "NEO HELIOPAN TS" by HAARMANN and REIMER, dibenzoylmethane derivatives: Butyl Methoxydibenzoylmethane sold in particular under the trademark "PARSOL 1789" by HOFFMANN LA ROCHE, Isopropyl Dibenzolylmethane, cinnamic derivatives: Ethylhexyl Methoxycinnamate sold in particular under the trademark "PARSOL MCX" by HOFFMANN LA ROCHE, Isopropyl Methoxy Cinnamate, Isoamyl Methoxy Cinnamate sold under the trademark "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, ββ'-diphenylacrylate derivatives: Octocrylene sold in particular under the trademark "UVINUL N539" by BASF, Etocrylene, sold in particular under the trademark "UVINUL N35" by BASF, benzophenone derivatives: Benzophenone-1 sold under the trademark "UVINUL 400" by BASF, Benzophenone-2 sold under the trademark "UVINUL D50" by BASF, Benzophenone-3 or Oxybenzone, sold under the trademark "UVINUL M40" by BASF, Benzophenone-4 sold under the trademark "UVINUL MS40" by BASF, Benzophenone-5, Benzophenone-6 sold under the trademark "HELISORB 11" by NORQUAY, Benzophenone-8 sold under the trademark "SPECTRA-SORB UV-24" by AMERICAN CYANAMID, Benzophenone-9 sold under the trademark "UVINUL DS-49" by BASF, Benzophenone-12, benzylidene camphor derivatives: 3-Benzylidene Camphor, 4-Methylbenzylidene Camphor sold under the name "EUSOLEX 6300" by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, phenylbenzimidazole derivatives: Phenylbenzimidazole Sulphonic Acid sold in particular under the trademark "EUSOLEX 232" by MERCK, Benzimidazilate sold under the trademark "NEO HELIOPAN AP" by HAARMANN and REIMER, triazine derivatives: Anisotriazine sold under the trademark "TINOSORB S" by CIBA GEIGY, Ethylhexyl triazones sold in particular under the trademark "UVINUL T150" by BASF, Diethylhexyl Butamido Triazone sold under the trademark "UVASORB HEB" by SIGMA 3V, phenylbenzotriazole derivatives: Drometrizole Trisiloxane sold under the name "SILATRIZOLE" by RHODIA CHIMIE, anthranilic derivatives: Menthyl anthranilate sold under the trademark "NEO HELIOPAN MA" by HAARMANN and REIMER, imidazoline derivatives: Ethylhexyl Dimethoxybenzylidene Dioxoimidazoline Propionate, benzalmalonate derivatives: Polyorganosiloxane with benzalmalonate functional groups sold under the trademark "PARSOL SLX" by HOFFMANN LA ROCHE, and mixtures thereof.

others: dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); uric and violuric acids; tannic acid and its derivatives (e.g., hexaethylether); (butyl carbotol) (6-propyl piperonyl)ether; hydroquinone;

The organic UV-screening agents which are more particularly preferred are chosen from the following compounds: Ethylhexyl Salicylate, Butyl Methoxydibenzoylmethane, Ethylhexyl Methoxycinnamate, Octocrylene, Phenylbenzimidazole Sulphonic Acid, Terephthalylidene Dicamphor Sulphonic, Benzophenone-3, Benzophenone-4, Benzophenone-5,4-Methylbenzylidene camphor, Benzimidazilate, Anisotriazine, Ethylhexyl triazone, Diethylhexyl Butamido Triazone, Methylene bis-Benzotriazolyl Tetramethylbutylphenol, Drometrizole Trisiloxane, and mixtures thereof.

Also preferred are the compositions described in U.S. Pat. No. 6,190,645 and in particular, sunscreen agents sold under the trademark INCROQUAT-UV-283 manufactured by Croda, Inc. The inorganic screening agents which may be used in the composition according to the invention are in particular nanopigments (mean size of the primary particles: generally between nm and 100 nm, preferably between 10 nm and 50 nm) of coated or uncoated metal oxides such as for example nanopigments of titanium oxide (amorphous or crystallized in the form of rutile and/or anatase), iron, zinc, zirconium or cerium oxides and mixtures thereof. Coating agents are moreover alumina and/or aluminum stearate. Such nanopigments of metal oxides, coated or uncoated, are in particular described in EP-A-0-518,772 and EP-A-0-518,773.

When used herein, the inorganic sunscreens are present in the amount of from about 0.1% to about 20%, preferably from about 0.5% to about 10%, more preferably from about 1% to about 5%, by weight of the composition.

15. Anti-Cellulite Agents

The compositions of the present invention may also comprise an anti-cellulite agent. Suitable agents may include, but are not limited to, xanthine compounds (e.g., caffeine, theophylline, theobromine, and aminophylline). In one embodiment, when anti-cellulite compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-cellulite compound.

Especially useful are combinations with the cellulite/slimming agents called Vexel™ (FR 2 654 619), Coaxel (FR 2 694 195), Cyclolipase™ (FR 2 733 149), Pleurimincyl™ and Lipocare™ (WO 98/43607) and Unislim™ (FR 0306063), all offered by SEDERMA.

16. Slimming, Toning or Draining Actives

The compositions can include one or more lipolytic agent selected among: phosphodiesterase inhibitors (e.g., xanthine derivatives), alpha-2 blockers compounds capable of blocking alpha-2 receptors at the adipocytes surface, beta-adrenergical agonists and antagonists (e.g. alverine and its organic or inorganic salts such as alverine citrate), agents inhibiting LDL and VLDL receptors synthesis, inhibitors of enzymes of fatty acid synthesis such as acetylCoA carboxylase, or fatty acid synthetase or cerulenine, compounds stimulating beta receptors and/or G proteins, glucose transport blockers such as serutine or rutine, neuropeptide Y (NPY) antagonists capable of blocking NPY receptors at the adipocytes surface, cAMP and its cosmetically acceptable derivatives, adenylate cyclase enzyme active agents such as forskolin, agents modifying fat acids transport, lipolytic peptides and lipolytic proteins, like peptides or proteins such as the peptides derived from the parathyroidal hormone, described in particular in the patents FR 2788058 and FR 2781231.

Others examples of usable lipolytic agents include botanical and marine extracts:

among plant extracts, there may more particularly be mentioned the extract of English ivy (*Hedera Helix*), of Chinese thorowax (*Bupleurum chinensis*), of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum Perforatum*), of butcher's-broom (*Ruscus aculeatus* L), of European meadowsweet (*Filipendula ulmaria* L), of big-flowered Jarva tea (*Orthosiphon Stamincus Benth*), of algae (*Fucus Vesiculosus*), of birch (*Betula alba*), of green tea, of cola nuts (*Cola Nipida*), of horse-chestnut, of bamboo, of spadeleaf (*Centella asiatica*), of heather, of fucus, of willow, of mouse-ear, extracts of escine, extracts of cangzhu, extracts of chrysanthellum indicum, extracts of the plants of the *Armeniacea* genus, *Atractylodis Platicodon, Sinnomenum, Pharbitidis, Flemingia*, extracts of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, extracts of *Guioa*, of *Davallia*, of *Terminalia*, of *Barringtonia*, of *Trema*, of antirobia, cecropia, argania, dioscoreae such as *Dioscorea opposita* or Mexican, as extracted of marine origin: extracts of algae or phytoplankton such as an extract of *Laminaria digitata*, diatoms, rhodysterol. All these extracts being able of course to be taken in mixtures.

17. The compositions according to the invention can also contain in addition one or more additional active selected among: agents acting on the microcirculation (vasculoprotectors or vasodilators) such as the natural flavonoids, ruscogenines, esculosides, escine, nicotinates, heperidine methyl chalcone, butcher's-broom, essential oils of lavender or rosemary, the extracts of *Ammi visnaga*; anti-glycation agents such as extracts of *Centella asiatica* and *Siegesbeckia*, silicium, amadorine, ergothioneine and its derivatives, hydroxystilbenes and their derivatives (e.g. resveratrol), vegetable extracts of the family of Ericaceae, in particular bilberry extracts (*Vaccinium angustifollium*), vitamin C and its derivatives, retinol and its derivatives.

Butylated Hydroxytoluene (BHT) and Butylated Hydroxyanisole (BHA)

The topical compositions of the present invention may comprise BHT or BHA.

In one embodiment, BHT and/or BHA is added from about 0.0001% to about 20% by weight of the composition, more preferably from about 0.001% to about 10%, even more preferably from about 0.01% to about 5%, and still more preferably from about 0.1% to about 0.5%.

18. Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

19. Desquamating/Keratolytic Actives

A desquamating/keratolytic active may be added to the compositions of the present invention. In one embodiment, the composition comprises from about 0.01% to about 10%, preferably from about 0.1% to about 5%, more preferably from about 0.5% to about 2%, by weight of the composition, of a desquamating/keratolytic active.

Examples of useful keratolytic and/or desquamating agents include urea, salicylic acid and alkyl derivatives thereof, saturated and unsaturated monocarboxylic acids, saturated and unsaturated bicarboxylic acids, tricarboxylic acids, alpha hydroxyacids and beta hydroxyacids of monocarboxylic acids, alpha hydroxyacids and beta hydroxyacids of bicarboxylic acids, alpha hydroxyacids and beta hydroxyacids of tricarboxylic acids, ketoacids, alpha ketoacids, beta ketoacids, of the polycarboxylic acids, of the polyhydroxy monocarboxylic acids, of the polyhydroxy bicarboxylic acids, of the polyhydroxy tricarboxylic acids.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2hydroxynonanoic acid; 2-hydroxydecanoic acid; 2-hydroxyundecanoic acid; 2-hydroxydodecanoic acid (alpha-hydroxylauric acid); 2-hydroxytetradecanoic acid (alpha-hydroxymyristic acid); 2-hydroxyhexadecanoic acid (alpha-hydroxypalmitic acid); 2-hydroxyoctadecanoic acid (alpha-hydroxystearic acid); 2-hydroxyeicosanoic acid (alpha-hydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyl lactic acid); 2-phenyl 2-methyl 2-hydroxyethanoic acid (atrolactic acid); 2-(4'-hydroxyphenyl)2-hydroxyethanoic acid; 2-(4'-chlorophenyl 2-hydroxyethanoic acid; 2-(3'-hydroxy-4'-methoxyphenyl)2-hydroxyethanoic acid; 2-(4'-hydroxy-3'-methoxyphenyl)2-hydroxyethanoic acid; 3'-(2-hydroxyphenyl)2-hydroxypropanoic acid; 3-(4'-hydroxyphenyl)2-hydroxypropanoic acid; and 2-(3',4'dihydroxyphenyl), and 2-hydroxyethanoic acid, 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Preferred keratolytic agents are selected from the group comprising glycolic acid, tartaric acid, salicylic acid, citric acid, lactic acid, pyruvic acid, gluconic acid, glucuronic acid, malic acid, mandelic acid, oxalic acid, malonic acid, succinic acid, acetic acid, phenol, resorcine, retinoic acid, adapalene, trichloroacetic acid, 5-fluoro uracil, azelaic acid. Keratolytic agents are also the salts, esters, possible cis or trans forms, racemic mixtures and/or the relative dextrorotatory or levorotatory forms of the above listed compounds. Such substances can be used singularly or in associations with each other.

Other keratolytic agents suitable for use herein can include enzymatic exfoliant based on a protease called Keratoline™ and offered by Sederma.

One desquamation system that is suitable for use herein comprises salicylic acid and zwitterionic surfactants and is described in U.S. Pat. No. 5,652,228. Another desquamation system that is suitable for use herein contains sulfhydryl compounds and zwitterionic surfactants and is described in U.S. Pat. No. 5,681,852. Zwitterionic surfactants such as those described in this referenced patent can also be useful as desquamatory agents herein, with cetyl betaine being particularly preferred.

20. Anti-Acne Actives

The compositions of the present invention can comprise one or more anti-acne actives. Examples of useful anti-acne actives include resorcinol, sulfur, erythromycin, salicylic acid, benzoyl peroxide, dehydroacetic acid and zinc. Further examples of suitable anti-acne actives are described in U.S. Pat. No. 5,607,980. Especially useful are combinations with the anti-acne ingredient called Ac.net™ offered by SEDERMA (WO 03/028692 A2).

In one embodiment, when anti-acne compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-acne compound.

21. Anti-Wrinkle Actives/Anti-Atrophy Actives

The compositions of the present invention can comprise a one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol, hydroxy acids (e.g., alpha-hydroxy acids such as lactic acid and glycolic acid or beta-hydroxy acids such as salicylic acid and salicylic acid derivatives such as the octanoyl derivative, lactobionic acid), keto acids (e.g., pyruvic acid), phytic acid, ascorbic acid (vitamin), stilbenes, cinnamates, resveratrol, kinetin, zeatin, dimethylaminoethanol, peptides from natural sources (e.g., soy peptides), and salts of sugar acids (e.g., Mn gluconate, Zn gluconate), lipoic acid; lysophosphatidic acid, skin peel agents (e.g., phenol and the like), vitamin B3 compounds and retinoids and other vitamin B compounds (e.g., thiamine (vitamin B1), pantothenic acid (vitamin B5), riboflavin (vitamin B2), and their derivatives and salts (e.g., HCL salts or calcium salts). Especially useful are combinations with the wrinkle agents called Dermolectine™ and Sterocare™ offered by SEDERMA (WO99/18927).

In one embodiment, when anti-wrinkle/anti-atrophy compounds are present in the compositions of the instant invention, the compositions comprise from about 0.0001% to about 50%, more preferably from about 0.001% to about 10%, still more preferably from about 0.01% to about 8%, and still more preferably from about 0.1% to about 5%, by weight of the composition, of the anti-wrinkle/anti-atrophy compound.

22. Anti-Oxidants/Radial Scavengers

The compositions of the present invention can include an anti-oxidant/radical scavenger. In one embodiment, the composition comprises from about 0.01% to about 10%, more preferably from about 0.1% to about 5%, of an anti-oxidant/radical scavenger.

Anti-oxidants/radical scavengers such as retinyl palmitate, ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, amines (e.g., N,N-diethylhydroxylamine, amino-guanidine), nordihydroguaiaretic acid, bioflavonoids, sulfhydryl compounds (e.g., glutathione), dihydroxy fumaric acid and its salts, lysine pidolate, arginine pilolate, amino acids, silymarin, lysine, 1-methionine, proline, superoxide dismutase, sorbic acids and its salts, lipoic acid, olive extracts, tea extracts, polyphenols such as proanthocyanidine from pine bark, carotenoids, curcumin compounds such as tetrahydrocurcumin, OCTA (L-2-oxo-4-thiazolidine carboxylic acid), glutathione, melanin, rosemary extracts and grape skin/seed extracts may be used. Preferred anti-oxidants/radical scavengers can be selected from esters of tocopherol, more preferably tocopherol acetate and tocopherol sorbate (U.S. Pat. No. 4,847,071)

23. Humectants, Moisturizers and Conditioning Agents

The compositions of the present invention can contain a safe and effective amount of a conditioning agent selected from, for example, humectants, moisturizers, and skin conditioners. A variety of these materials can be employed and in one embodiment can be present at a level of from about 0.01% to about 20%, more preferably from about 0.1% to about 10%, and still more preferably from about 0.5% to about 7%, by weight of the composition. These materials can include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose), starches, sugar and starch derivatives (e.g., alkoxylated glucose, fructose, glucosamine), hyaluronic acid, lactamide monoethanolamine, acetamide monoethanolamine, panthenol, allantoin, petroleum and mixtures thereof. Also useful herein are the propoxylated glycerols described in U.S. Pat. No. 4,976,953.

Also useful are various C1-C30 monoesters and polyesters of sugars and related materials. These esters are derived from a sugar or polyol moiety and one or more carboxylic acid moieties.

Preferably, the conditioning agent is selected from urea, guanidine, sucrose polyester, panthenol, dexpanthenol, allantoin, glycerol, and combinations thereof.

Humectants can be selected from the group consisting of polyhydric alcohols, water soluble alkoxylated nonionic polymers, and mixtures thereof. Polyhydric alcohols useful herein include polyhdroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, PPG-12/SMDI copolymer and mixtures thereof.

24. Active Oxygen Generation Inhibitors

The compositions of the present invention may also comprise a an active oxygen generation inhibitor selected from the group comprising quercetin, rutin, taxifolin, kaempferol, myricetin, curcumin, resveratrol, arecoline, apigenin, wogonin, luteolin, tectorigenin, and a mixture thereof.

This active oxygen generation inhibitor may be contained in an amount of about 0.001% to about 5%, more preferably in an amount of about 0.01% to about 3%%, by weight of the composition.

25. Chelators

The compositions of the present invention may also comprise a chelator or chelating agent. As used herein, "chelator" or "chelating agent" means an active agent capable of removing a metal ion from a system by forming a complex so that the metal ion cannot readily participate in or catalyze oxygen radical formation. In one embodiment, a chelating agent is added to a composition of the present invention, preferably from about 0.00001% to about 10%, more preferably from about 0.001% to about 5%, by weight of the composition. Exemplary chelators that are useful herein include those that are disclosed in U.S. Pat. No. 5,487,884, WO 91/16035 and WO 91/16034. Examples of chelating agents include N-hydroxysuccinimide, EDTA, Disodium EDTA, NTA, deferoxamine, hydroxamic acids and their salts, phytic acid, phytate, gluconic acid and its salts, transferrine, lactoferrin; furildioxime and derivatives thereof.

26. Anti-Inflammatory Agents

An anti-inflammatory agent may be added to the compositions of the present invention. In one embodiment, an anti-inflammatory agent is added at a level of from about 0.01% to about 10%, preferably from about 0.5% to about 5%, by weight of the composition. The exact amount of anti-inflammatory agent to be used in the compositions will depend on the particular anti-inflammatory agent utilized since such agents vary widely in potency Steroidal anti-inflammatory agents can include, but are not limited to, corticosteroids such as hydrocortisone. In addition, nonsteroidal anti-inflammatory agents can be useful herein. The varieties of compounds encompassed by this group are well known to those skilled in the art. Specific non-steroidal anti-inflammatory agents that can be useful in the composition of the present invention include, but are not limited to, oxicams such as piroxicam, salicylates such as aspirin; acetic acid derivatives, such as felbinac, fenamates, such as etofenamate, flufenamic, mefenamic, meclofenamic, acids; propionic acid derivatives, such as ibuprofen, naproxen, pyrazoles, and mixtures thereof. Mixtures of these non-steroidal anti-inflammatory agents may also be employed, as well as the dermatologically acceptable salts and esters of these agents. Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper methysticum* extract (Kava Kava from SEDERMA (FR 2 771 002 and WO 99/25369), *Bacopa monieri* extract (Bacocalmine™ from SEDERMA, WO 99/40897) and sea whip extract, may be used. Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred. Additional anti inflammatory agents include diosgenol, saponines, sapogenines, lignanes, triterpenes saponosides and genines.

27. Tanning Actives

The compositions of the present invention can comprise a tanning active. In one embodiment, the composition comprises from about 0.1% to about 20%, more preferably from about 2% to about 7%, and even more preferably from about 3% to about 6%, by weight of the composition, of a tanning active. A preferred tanning active is dihydroxyacetone, which is also known as DHA or 1,3-dihydroxy-2-propanone. Especially useful are combinations with the tanning agents called Tyr-ol™ and Tyr-excel™ offered by SEDERMA and described in Fr 2 702 766 and WO 03/017966 respectively.

28. Skin Lightening Agents

The compositions of the present invention may contain a skin lightening agent. When used, the compositions preferably contain from about 0.001% to about 10%, more preferably from about 0.02% to about 5%, also preferably from about 0.05% to about 2%, by weight of the composition, of a skin lightening agent. Suitable skin lightening agents include those known in the art, including kojic acid, hydroquinone, aminophenol derivatives, N-cholesteryloxycarbonyl-para-aminophenol and N-ethyloxycarbonyl-para-aminophenol; iminophenol derivatives, L-2-oxothiazolidine-4-carboxylic acid or procysteine, and also its salts and esters, arbutin, tranexamic acid, ascorbic acid and derivatives thereof (e.g., magnesium ascorbyl phosphate or sodium ascorbyl phosphate, ascorbyl glucoside and the like (such as AA2G from Hayashibara)), and extracts (e.g., mulberry extract, placental extract, skullcap extract broussonetia extract, oil soluble liquorice extract (such as these available from Maruzen), oil soluble liquorice extract (glycyrrhiza, chamomile extract (such as these available from Kao)), m-Tranexamic acid/vitamin C ethyl (such as these available from Shiseido), adenosine monophosphate disodium (APM offered by Otsuka), ellagic acid (Lion), rucinol (Pola), ethyl ascorbyl ether). Skin lightening agents suitable for use herein also include those described in WO95/34280, PCT/US 95/07432, co-pending. U.S. Ser. No. 08/390,152 and PCT/US 95/23780. Especially useful are combinations with the skin lightening agents called Melaclear™, Etioline™, Melaslow™ and Lumiskin™ offered by SEDERMA and described respectively in FR 2 732 215, WO 98/05299, WO 02/15871 and PCT/FR 03/02400. Other skin lightening materials suitable for use herein can include Actiwhite® (Cognis), Emblica® (Rona), Azeloglicina (Sinerga) and Sepiwhite®(Seppic). A preferred skin lightening agent is ascorbyl glucoside.

29. Antimicrobial, Antibacterial and Antifungal Actives

The compositions of the present invention can comprise one or more anti-fungal or anti-microbial actives. A safe and effective amount of an antimicrobial or antifungal active can be added to the present compositions. In one embodiment, the composition comprises from about 0.001% to about 10%, preferably from about 0.01% to about 5%, and more preferably from about 0.05% to about 2%, by weight of the composition, of an antimicrobial or antifungal active. Suitable anti-microbial actives include coal tar, sulfur, whitfield's ointment, castellani's paint, aluminum chloride, gentian violet, octopirox (piroctone olamine), 3,4,4'-trichlorocarbanilide (trichlosan), triclocarban, ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazolinone and azoles, and combinations thereof. Preferred anti-microbials include itraconazole, ketoconazole, selenium sulphide and coal tar. In one embodiment, one or more anti-fungal or anti-microbial active is combined with an anti-dandruff active selected from polyvalent metal salts of pyrithione.

a. Azoles

Azole anti-microbials include imidazoles such as benzimidazole, benzothiazole, bifonazole, butoconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein are ketoconazole and climbazole.

b. Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5 c. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

d. Additional Anti-Microbial Actives

Additional anti-microbial actives of the present invention may include one or more keratolytic agents such as salicylic acid, extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

Preferred examples of actives useful herein include those selected from the group consisting of benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, phytic acid, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, miconazole, ketoconazole, neomycin sulfate, and mixtures thereof.

Especially useful are combinations with the ingredient range called OSMOCIDE™ offered by SEDERMA (WO 97/05856).

30. Thickening Agents (Including Thickeners and Gelling Agents)

The compositions of the present invention can comprise one or more thickening agents. In one embodiment, a thickening agent is present at a level of from about 0.05% to about 10%, preferably from about 0.1% to about 5%, and more preferably from about 0.25% to about 4%, by weight of the composition. Nonlimiting classes of thickening agents include those selected from the following:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, U.S. Pat. No. 4,509,949, U.S. Pat. No. 2,798,053, and in CTFA International Cosmetic Ingredient Dictionary, Tenth Edition, 2004. Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Godrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, U.S. Pat. No. 4,849,484, U.S. Pat. No. 4,835,206, U.S. Pat. No. 4,628,078 U.S. Pat. No. 4,599,379 and EP 228,868.

c. Polyacrylamide Polymers

The compositions of the present invention can optionally contain polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties and may be used in concentration ranges between 1 and 99%, most advantageously between 5 and 15%.

d. Polysaccharides

A wide variety of polysaccharides can be useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™ CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

31. Antiperspirant Actives

Antiperspirant actives may also be included in the compositions of the present invention. Suitable antiperspirant actives include astringent metallic salts, especially the inorganic and organic salts of aluminum zirconium and zinc, as well as mixtures thereof. Particularly preferred are the aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof. In one embodiment, when antiperspirant actives are present in the compositions of the instant invention, the compositions comprise from about 0.01% to about 50%, more preferably from about 0.1% to about 40%, and still more preferably from about 1% to about 30%, by weight of the composition, of the antiperspirant compound.

32. Detersive Surfactants

The compositions of the present invention can include detersive surfactant from about 1% to about 90%, more preferably from about 5% to about 10%. The detersive surfactant component can be included to provide cleaning performance to the composition. The detersive surfactant component in turn can comprise anionic detersive surfactant, zwitterionic or amphoteric detersive surfactant, or a combination thereof. Suitable anionic detersive surfactant components for use in the composition herein include those which are known for use in hair care or other personal care cleansing compositions. When included, the concentration of the anionic surfactant component in the composition can preferably be sufficient to provide the desired cleaning and lather performance, and generally can range from about 5% to about 50%, preferably from about 8% to about 30%, more preferably from about 10% to about 25%, even more preferably from about 12% to about 22%.

Preferred anionic surfactants suitable for use in the compositions are the alkyl and alkyl ether sulfates. Other suitable anionic detersive surfactants are the water-soluble salts of organic, sulfuric acid reaction products, alkoyl isethionates, sodium or potassium salts of fatty acid amides of methyl tauride, olefin sulfonates, and beta-alkyloxy alkane sulfonates.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. Nos. 5,104,646 and 5,106,609. Amphoteric detersive surfactants include derivatives of aliphatic secondary and tertiary amines. The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M.C. Publishing Co., and U.S. Pat. Nos. 3,929,678, 2,658,072; 2,438,091; 2,528,378.

33. Cationic, Anionic and Amphoteric Polymers

The compositions of the present invention can comprise polymers which may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or non-ionic.

When included, concentrations of the cationic polymer in the composition can typically range from about 0.05% to about 3%, preferably from about 0.075% to about 2.0%, more preferably from about 0.1% to about 1.0 a. Cationic Polymers

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate. Non limiting examples of such polymers are described in the CTFA.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyltriethylammonium bromide; amine derivatives of methacrylic acid or amine derivatives of methacrylamide derived from methacrylic acid or methacrylamide and a dialkylalkanolamine having C1-C6 alkyl groups such as dimethylaminoethyl (meth)acrylate, diethylaminoethyl(meth)acrylate, dimethylaminopropyl(meth)acrylate, or dimethylaminopropyl(meth)acrylamide.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. A non limiting example is polymethyacrylamidopropyl trimonium chloride, available under the tradename Polycare 133, from Rhone-Poulenc.

Other suitable cationic polymers for use in the composition include polysaccharide polymers, such as cationic cellulose derivatives and cationic starch derivatives.

Preferred cationic cellulose polymers are salts of hydroxyethyl cellulose reacted with trimethyl ammonium substituted epoxide, referred to in the industry (CTFA) as Polyquaternium 10 and available from Amerchol Corp. in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

b. Anionic Polymers

Examples of anionic polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

c. Amphoteric Monomers

Examples of the amphoteric monomers include zwitterionized derivatives of the aforementioned amine derivatives of (meth)acrylic acids or the amine derivatives of (meth)acrylamide such as dimethylaminoethyl(meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

34. Nonionic Polymers

The compositions herein can comprise nonionic polymers. For instance, polyalkylene glycols having a molecular weight of more than about 1000 can be used. Preferred polyethylene glycol polymers can include PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Examples of nonionic monomers are acrylic or methacrylic acid esters of C1-C24 alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene, chlorostyrene, vinyl esters such as vinyl acetate, vinyl chloride, vinylidene chloride, acrylonitrile, alpha-methylstyrene, t-butylstyrene, butadiene, cyclohexadiene, ethylene, propylene, vinyl toluene, alkoxyalkyl(meth)acrylate, methoxy ethyl(meth)acrylate, butoxyethyl(meth)acrylate, allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl(meth)acrylate, n-butyl methacrylate, isobutyl methacrylate, 2-ethylhexyl methacrylate, methyl methacrylate, t-butylacrylate, t-butylmethacrylate, and mixtures thereof.

35. Hair Conditioning Agents

Conditioning agents include any material which is used to give a particular conditioning benefit to keratinous tissue. For instance, in hair treatment compositions, suitable conditioning agents include those which deliver one or more benefits relating to shine, softness, combability, antistatic properties, wet-handling, damage, manageability, body, and greasiness. Conditioning agents useful in the compositions of the present invention can comprise a water insoluble, water dispersible, non-volatile liquid that forms emulsified, liquid particles. Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

When included, the concentration of the conditioning agent in the composition can be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

a. Silicones

The conditioning agent of the compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair. The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

b. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

c. Amino and Cationic Silicones

Cationic silicone fluids suitable for use in the compositions of the present invention include, but are not limited to, the polymer known as "trimethylsilylamodimethicone".

Other silicone cationic polymers which may be used in the compositions of the present invention may be UCARE SILICONE ALE 56™, available from Union Carbide.

d. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane)(methylvinylsiloxane) copolymer, poly(dimethylsiloxane)(diphenyl siloxane)(methylvinylsiloxane)copolymer and mixtures thereof.

e. High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

f. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

36. Organic Conditioning Oils

Compositions of the present invention may also comprise organic conditioning oil. In one embodiment, from about 0.05% to about 20%, preferably from about 0.08% to about 1.5%, more preferably from about 0.1% to about 1%, of at least one organic conditioning oil is included as a conditioning agent, either alone or in combination with other conditioning agents, such as the silicones (described herein).

a. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C12 to about C19. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2, 2, 4,4,6,6-dimethyl-8-methylnonane, available from Permethyl Corporation, hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

b. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of C4 to about C14 olefenic monomers, preferably from about C6 to about C12.

Preferred non-limiting examples of olefenic monomers for use in preparing the polyolefin liquids herein include ethylene, propylene, 1-butene, 1-pentene, 1-hexene to 1-hexadecenes, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

c. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters.

Specific non-limiting examples of suitable synthetic fatty esters for use in the compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

37. Anti-Dandruff Actives

The compositions of the present invention may also contain an anti-dandruff agent. Suitable, non-limiting examples of anti-dandruff particulates include: pyridinethione salts, azoles, selenium sulfide, particulate sulfur, and mixtures thereof. Preferred are pyridinethione salts, especially 1-hydroxy-2-pyridinethione salts. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"). Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

38. Humectant

The compositions of the present invention may contain a humectant. Humectants can be selected from the group consisting of polyhydric alcohols, water soluble alkoxylated nonionic polymers, and mixtures thereof. Humectants, when used herein, are preferably used at levels of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as PEG-200, PEG-400, PEG-600, PEG-1000 (CTFA names), and mixtures thereof.

39. Suspending Agent

The compositions of the present invention may further comprise a suspending agent, preferably at concentrations effective for suspending water-insoluble material in dispersed form in the compositions or for modifying the viscosity of the composition. Such concentrations can preferably range from about 0.1% to about 10%, more preferably from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, nitro cellulose, sodium carboxymethyl cellulose, crystalline cellulose, cellulose powder, polyvinylpyrrolidone, polyvinyl alcohol, guar gum, hydroxypropyl guar gum, arabia gum, galactan, carob gum, pectin, agar, quince seed (*Cyclonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid. Actives aforementioned as thickening agents can also be used herein as suspending agents.

Commercially available viscosity modifiers highly useful herein include Carbomers with tradenames Carbopol 934, Carbopol 940, Carbopol 950, Carbopol 980, and Carbopol 981, all available from B.F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, long chain acyl derivatives and mixtures thereof. These suspending agents are described in U.S. Pat. No. 4,741,855. These preferred suspending agents include ethylene glycol esters of fatty acids, alkanol amides of fatty acids, long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® available from Rheox, Inc.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

40. Terpene Alcohol

The compositions of the present invention may comprise a terpene alcohol or combinations of terpene alcohols. As used herein, "terpene alcohol" refers to organic compounds composed of two or more 5-carbon isoprene units [CH2=C(CH=3)-CH=CH2] with a terminal hydroxyl group. Preferably, the composition can comprise from about 0.001% to about 50%, preferably from about 0.01% to about 20%, more preferably from about 0.1% to about 15%, even more preferably from about 0.1% to about 10%, still more preferably from about 0.5% to about 5%, and still more preferably from about 1% to about 5%, by weight of the composition, of the terpene alcohol.

Examples of terpene alcohols that can be useful herein include farnesol, derivatives of farnesol, isomers of farnesol, geraniol, derivatives of geraniol, isomers of geraniol, phytantriol, derivatives of phytantriol, isomers of phytantriol, and mixtures thereof. A preferred terpene alcohol for use herein is farnesol.

a. Farnesol and Derivatives Thereof.

Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco) and trans-trans-farnesol (Sigma Chemical Company). A suitable derivative of farnesol is farnesyl acetate which is commercially available from Aldrich Chemical Company.

b. Geraniol and Derivatives Thereof.

Geraniol is the common name for the chemical known as 3,7-dimethyl-2,6-octadien-1-ol. As used herein, "geraniol" includes isomers and tautomers of such. Geraniol is commercially available from Aldrich Chemical Company. Suitable derivatives of geraniol include geranyl acetate, geranylgeraniol, geranyl pyrophosphate, and geranylgeranyl pyrophosphate, all of which are commercially available from Sigma Chemical Company. For example, geraniol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

c. Phytantriol and Derivatives Thereof.

Phytantriol is the common name for the chemical known as 3,7,11,15 tetramethylhexadecane-1,2,3,-triol. Phytantriol is commercially available from BASF. For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

II. CARRIER

The compositions of the present invention can comprise an orally or a dermatologically acceptable carrier, or injectible liquid, depending upon the desired product form.

A. Dermatologically Acceptable Carrier

The topical compositions of the present invention can also comprise a dermatologically acceptable carrier for the composition. In one embodiment, the carrier is present at a level of from about 50% to about 99.99%, preferably from about 60% to about 99.9%, more preferably from about 70% to about 98%, and even more preferably from about 80% to about 95%, by weight of the composition.

The carrier can be in a wide variety of forms. Non-limiting examples include simple solutions (water or oil based), emulsions, and solid forms (gels, sticks). For example, emulsion carriers can include, but are not limited to, oil-in-water, water-in-oil, water-in-silicone, water-in-oil-in-water, and oil-in-water-in-silicone emulsions.

Depending upon the desired product form, preferred carriers can comprise an emulsion such as oil-in-water emulsions (e.g., silicone in water) and water-in-oil emulsions, (e.g., water-in-silicone emulsions). As will be understood by the skilled artisan, a given component will distribute primarily into either the water or oil phase, depending on the water solubility/dispensability of the component in the composition. In one embodiment, oil-in-water emulsions are especially preferred.

Emulsions according to the present invention can contain an aqueous phase and a lipid or oil. Lipids and oils may be derived from animals, plants, or petroleum and may be natural or synthetic (i.e., man-made). Preferred emulsions can also contain a humectant, such as glycerin. Emulsions can further comprise from about 0.1% to about 10%, more preferably from about 0.2% to about 5%, of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and McCutcheon's Detergents and Emulsifiers, North American Edition, pages 317-324 (1986). Suitable emulsions may have a wide range of viscosities, depending on the desired product form.

The compositions of the present invention can be in the form of pourable liquids (under ambient conditions). The compositions can therefore comprise an aqueous carrier, which is typically present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

The emulsion may also contain an anti-foaming agent to minimize foaming upon application to the keratinous tissue. Anti-foaming agents include high molecular weight silicones and other materials well known in the art for such use.

Preferred water-in-silicone and oil-in-water emulsions are described in greater detail below.

1. Water-in-Silicone Emulsion

Water-in-silicone emulsions can contain a continuous silicone phase and a dispersed aqueous phase.

a. Continuous Silicone Phase

Preferred water-in-silicone emulsions of the present invention can contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter. The continuous silicone phase contains a polyorganosiloxane oil. A preferred water-in-silicone emulsion system is formulated to provide an oxidatively stable vehicle for the active ingredients of the present invention. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid, Dow Corning® 225 fluid, and Dow Corning® 200 fluids Examples of suitable alkyl-substituted dimethicones include cetyl dimethicone and lauryl dimethicone.

Cyclic polyalkylsiloxanes suitable for use in the composition include commercially available cyclomethicones such as Dow Corning® 244 fluid, Dow Corning® 344 fluid, Dow Corning®245 fluid and Dow Corning® 345 fluid.

Also useful are materials such as trimethylsiloxysilicate. A commercially available trimethylsiloxysilicate is sold as a mixture with dimethicone as Dow Corning® 593 fluid. Dimethiconols are also suitable for use in the composition. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful. Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

b. Dispersed Aqueous Phase

The topical compositions of the present invention can contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelating ingredients, gums, water-soluble or dispersible alcohols and polyols, buffers, preservatives, sunscreening agents, colorings, and the like.

The topical compositions of the present invention will typically contain from about 25% to about 90%, preferably from about 40% to about 80%, more preferably from about 60% to about 80%, water in the dispersed aqueous phase by weight of the composition.

c. Emulsifier for Dispersing the Aqueous Phase

The water-in-silicone emulsions of the present invention may preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present invention, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

Nonlimiting examples of dimethicone copolyols and other silicone surfactants useful as emulsifiers herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Dimethicone copolyol emulsifiers useful herein are described, for example, in U.S. Pat. No. 4,960,764, EP 330, 369. Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681; U.S. Pat. No. 4,421,769; and U.S. Pat. No. 3,755, 560.

Nonlimiting examples of these non-silicon-containing emulsifiers include: polyethylene glycol sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

d. Silicone Elastomer

The compositions of the present invention may also include from about 0.1% to about 30%, by weight of the composition, of a silicone elastomer component. Preferably, the composition includes from about 1% to about 30%, more preferably from about 2% to about 20%, by weight of the composition, of the silicone elastomer component.

Suitable for use herein are silicone elastomers, which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Addition reaction-curing organopolysiloxane compositions are preferred for their rapid curing rates and excellent uniformity of curing. A particularly preferred addition reaction-curing organopolysiloxane composition is prepared from: a) an organopolysiloxane having at least 2 lower alkenyl groups in each molecule; b) an organopolysiloxane having at least 2 silicon-bonded hydrogen atoms in each molecule; and c) a platinum-type catalyst.

The compositions of the present invention may include an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomers can notably be chosen from the crosslinked polymers described in U.S. Pat. Nos. 5,412,004, 5,837,793, and 5,811,487. In addition, an emulsifying elastomer comprised of dimethicone copolyol crosspolymer (and) dimethicone is available from Shin Etsu under the tradename KSG-21.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16,18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. No. 4,970,252, U.S. Pat. No. 5,760,116, and U.S. Pat. No. 5,654,362.

Commercially available elastomers preferred for use herein are Dow Corning's 9040 silicone elastomer blend, Shin Etsu's KSG-21, and mixtures thereof.

e. Carrier for Silicone Elastomer

The topical compositions of the present invention may include from about 1% to about 80%, by weight of the composition, of a suitable carrier for the for the crosslinked organopolysiloxane elastomer component described above. The carrier, when combined with the cross-linked organopolysiloxane elastomer particles of the present invention, serves to suspend and swell the elastomer particles to provide an elastic, gel-like network or matrix. The carrier for the cross-linked siloxane elastomer is liquid under ambient conditions, and preferably has a low viscosity to provide for improved spreading on the skin.

Concentrations of the carrier in the cosmetic compositions of the present invention will vary primarily with the type and amount of carrier and the cross-linked siloxane elastomer employed. Preferred concentrations of the carrier are from about 5% to about 50%, more preferably from about 5% to about 40%, by weight of the composition.

The carrier for the cross-linked siloxane elastomer includes one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The term "volatile" as used herein refers to all materials that are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 (cal/cm3>) 05.

f. Non-Polar, Volatile Oils

The composition of the present invention may include non-polar, volatile oils. The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. Examples of preferred non-polar, volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals). Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

g. Relatively Polar, Non-Volatile Oils

The composition of the present invention may include relatively polar, non-volatile oils. The non-volatile oil is "relatively polar" as compared to the non-polar, volatile oil discussed above. Therefore, the non-volatile co-carrier is more polar (i.e., has a higher solubility parameter) than at least one of the non-polar, volatile oils. Relatively polar, non-volatile oils potentially useful in the present invention are disclosed, for example, in Cosmetics, Science, and Technology, Vol. 1, 27-104 edited by Balsam and Sagarin, 1972; U.S. Pat. Nos. 4,202,879 and 4,816,261. Relatively polar, non-volatile oils useful in the present invention are preferably selected from silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof.

h. Non-Polar, Non-Volatile Oils

In addition to the liquids discussed above, the carrier for the cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. Nos. 4,202,879 and 4,816,261. The non-volatile oils useful in the present invention are essentially non-volatile polysiloxanes, paraffinic hydrocarbon oils, and mixtures thereof.

2. Oil-in-Water Emulsions

Other preferred topical carriers include oil-in-water emulsions, having a continuous aqueous phase and a hydrophobic, water-insoluble phase ("oil phase") dispersed therein. The "oil phase" can contain oil, silicone or mixtures thereof, and includes but is not limited to the oils and silicones described above in the section on water-in-oil emulsions. The distinction of whether the emulsion is characterized as an oil-in-water or silicone-in-water emulsions is a function of whether the oil phase is composed of primarily oil or silicone. The water phase of these emulsions consists primarily of water, but can also contain various other ingredients such as those water phase ingredients listed in the above section on water-in-oil emulsion. The preferred oil-in-water emulsions comprises from about 25% to about 98%, preferably from about 65% to about 95%, more preferably from about 70% to about 90% water by weight of the total composition.

In addition to a continuous water phase and dispersed oil or silicone phase, these oil-in-water compositions also comprise an emulsifier to stabilize the emulsion. Emulsifiers useful herein are well known in the art, and include nonionic, anionic, cationic, and amphoteric emulsifiers. Non-limiting examples of emulsifiers useful in the oil-in-water emulsions of this invention are given in McCutcheon's, *Detergents and Emulsifiers*, North American Edition (1986), U.S. Pat. No. 5,011,681; U.S. Pat. No. 4,421,769; and U.S. Pat. No. 3,755,560. Examples of suitable oil-in-water emulsion carriers are described in U.S. Pat. No. 5,073,371, and U.S. Pat. No. 5,073,372. An especially preferred oil-in-water emulsion, containing a structuring agent, hydrophilic surfactant and water, is described in detail hereinafter.

a. Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention contain from about 0.5% to about 20%, more preferably from about 1% to about 10%, even more preferably from about 1% to about 5%, by weight of the composition, of a structuring agent.

The preferred structuring agents of the present invention include stearic acid, palmitic acid, stearyl alcohol, cetyl alcohol, behenyl alcohol, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

b. Hydrophilic Surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from nonionic surfactants. Among the nonionic surfactants that are useful herein are those that can be broadly defined as condensation products of long chain alcohols, e.g. C8-30 alcohols, with sugar or starch polymers, i.e., glycosides.

These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids), the condensation products of alkylene oxides with 2 moles of fatty acids (i.e. alkylene oxide diesters of fatty acids), the condensation products of alkylene oxides with fatty alcohols (i.e. alkylene oxide ethers of fatty alcohols), the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants. An especially preferred surfactant corresponding to the above structure is coconut alkyl N-methyl glucoside amide. Processes for making compositions containing polyhydroxy fatty acid amides are disclosed, for example in U.S. Pat. No. 2,965,576; U.S. Pat. No. 2,703,798, and U.S. Pat. No. 1,985,424.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate. This is commercially available from ICI under the tradename Arlatone 2121.

Other suitable surfactants useful herein include a wide variety of cationic, anionic, zwitterionic, and amphoteric surfactants such as are known in the art and discussed more fully below. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds, examples of which are described in U.S. Pat. No. 5,151,209; U.S. Pat. No. 5,151,210; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's, *Detergents & Emulsifiers*, (North American edition 1979) M.C. Publishing Co.; and Schwartz, et al., *Surface Active Agents, Their Chemistry and Technology*, New York: Interscience Publishers, 1949.

Nonlimiting examples of these cationic emulsifiers include cetearyl olivate, sorbitan olivate, stearamidopropyl PG-dimonium chloride phosphate, behenamidopropyl PG dimonium chloride, stearamidopropyl ethyldimonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C30 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow)dimethyl ammonium chloride, di(hydrogenated tallow)dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintain to enhance physical and chemical stability, especially when such a combination contains ionic and/or highly polar solvents.

A wide variety of anionic surfactants can also be useful herein. Nonlimiting examples of anionic surfactants include the alkoyl isethionates, and the alkyl and alkyl ether sulfates. The reaction products of fatty acids esterified with isethianonic acid and neutralized, i.e. the alkoyl isethionates typically have the formula RCO—OCH$_2$CH$_2$SO$_3$ M wherein R is alkyl or alkenyl of from about 10 to about 30 carbon atoms, and M is a water-soluble cation such as ammonium, sodium, potassium and triethanolamine. For example, the fatty acids are derived from coconut or palm kernel oil. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof. Also suitable are salts of fatty acids, amids of methyl taurides. Other similar anionic surfactants are described in U.S. Pat. Nos. 2,486,921; 2,486,922 and 2,396,278.

The alkyl and alkyl ether sulfates typically have the respective formulae ROSO$_3$ M and RO(C$_2$H$_4$O)xSO$_3$M, wherein R is alkyl or alkenyl of from about 10 to about 30 carbon atoms, x is from about 1 to about 10, and M is a water-soluble cation such as ammonium, alkanolamines such as triethanolamine, monovalent metals, such as sodium and potassium, and polyvalent metal cations such as magnesium and calcium. Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized Another suitable class of anionic surfactants are the water-soluble salts of the organic, sulfuric acid reaction products of the general formula: R1-SO$_3$—M wherein R1 is chosen from the group including a straight or branched chain, saturated aliphatic hydrocarbon radical having from about 8 to about 24, preferably about 10 to about 16, carbon atoms; and M is a cation described hereinbefore. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate. Other anionic surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid. Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions are the beta-alkyloxy alkane sulfonates. These surfactants conform to the formula

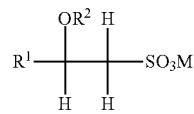

where R1 is a straight chain alkyl group having from about 6 to about 20 carbon atoms, R$^2$ is a lower alkyl group having from about 1 to about 3 carbon atoms, preferably 1 carbon atom, and M is a water-soluble cation as described hereinbefore. Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH$_2$)mCO$_2$M]$_2$ and RNH(CH$_2$)mCO$_2$ M wherein m is from 1 to 4, R is a C8-C22 alkyl or alkenyl, and M is H, alkali metal, alkaline earth metal ammonium, or alkanolammonium. Preferred amphoteric surfactants for use in the present invention include cocoamphoacetate, cocoamphodiacetate, lauroamphoacetate, lauroamphodiacetate, and mixtures thereof. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072; N-higher alkyl aspartic acids such as those produced according to the teaching of U.S. Pat. No. 2,438,091; and the products sold under the tradename "Miranol" and described in U.S. Pat. No. 2,528,378. Other examples of useful amphoterics include phosphates, such as coamidopropyl PG-dimonium chloride phosphate (commercially available as Monaquat PTC, from Mona Corp.).

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2$ M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

c. Water Emollient

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients is known and may be used herein. Sagarin, *Cosmetics, Science and Technology,* 2nd Edition, Vol. 1, pp. 32-43 (1972) contains numerous examples of materials suitable as an emollient. A preferred emollient is glycerin. Glycerin is preferably used in an amount of from about 0.001 to about 30%, more preferably from about 0.01 to about 20%, still more preferably from about 0.1 to about 10%, e.g., 5%.

Lotions and creams according to the present invention generally contain a solution carrier system and one or more emollients. Lotions and creams typically contain from about 1% to about 50%, preferably from about 1% to about 20%, of emollient; from about 50% to about 90%, preferably from about 60% to about 80%, water; the polypeptides, according to the invention, and the additional skin care active (or actives) in the above described amounts. Creams are generally thicker than lotions due to higher levels of emollients or higher levels of thickeners.

Ointments of the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, *Cosmetics, Science and Technology,* 2nd Edition, Vol. 1, pp. 72-73 (1972), and/or an emollient. For example, an ointment may contain from about 2% to about 10% of an emollient; from about 0.1% to about 2% of a thickening agent; and the polypeptide and the additional skin care active (or actives) in the above described amounts.

Compositions of this invention useful for cleansing ("cleansers") can be formulated with a suitable carrier, e.g., as described above, and preferably comprise from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197 for exemplary surfactants useful herein. Examples of a broad variety of additional surfactants useful herein are described in McCutcheon's *Detergents and Emulsifiers*, North American Edition (1986), published by Allured Publishing Corporation. The cleansing compositions can optionally contain, at their art-established levels, other materials which are conventionally used in cleansing compositions.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier and may include conventional ingredients such as oils, colorants, pigments, emollients, fragrances, waxes, stabilizers, and the like. Exemplary carriers and such other ingredients which are suitable for use herein are described, for example, in WO96/33689, and GB 2274585.

B. Orally Acceptable Carrier

The compositions of the present invention can also comprise an orally acceptable carrier if they are to be ingested. Any suitable orally ingestible carrier or carrier form, as known in the art or otherwise, can be used. Non-limiting examples of oral personal care compositions can include, but are not limited to, tablets, pills, capsules, drinks, beverages, syrups, granules, powders, vitamins, supplements, health bars, candies, chews, and drops.

C. Injectible Liquid

The compositions of the present invention can also comprise a liquid that is acceptable for injection in and/or under the skin if the composition is to be injected. Any suitable acceptable liquid as known in the art or otherwise can be used.

III. COMPOSITION PREPARATION

The compositions useful for the methods of the present invention are generally prepared by conventional methods such as are known in the art of making topical and oral compositions and compositions for injection. Such methods typically can involve mixing of the ingredients in one or more steps to a relatively uniform state, with or without heating, cooling, application of vacuum, and the like.

The physical form of the compositions according to the invention is not important: creams, lotions, ointments, milks, gels, emulsions, dispersions, solutions, suspensions, cleansers, foundations, anhydrous preparations (sticks, in particular lipsticks, body and bath oils), shower and bath gels, shampoos and scalp treatment lotions, cream or lotion for care of the skin or hair, sun-screen lotions, milks or creams, artificial suntan lotions, creams or milks, shaving creams or foams, aftershave lotions, mascaras or nail varnishes, lipsticks, skin "essences," serums, adhesive or absorbent materials, transdermal patches, powders, emolient lotion, emollient milk, emollient cream, sprays, oils for the body and the bath, foundation tint bases, pomade, colloid, compact or solid suspension, pencil, sprayable formulation, brossable, make-up, rouge, blush, eyeliner, lipliner, lip gloss, facial or body powder, mousse, styling gels, nail conditioner, brush on formulation, lip balms, skin conditioners, cold creams, moisturizers, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, rinses, nose sprays and so on. These compositions can also be presented in the form of lipsticks intended to apply colour or to protect the lips from cracking, or of make-up products for the eyes or tints and tint bases for the face. Compositions in accordance with the invention include cosmetics, personal care products and pharmaceutical preparations. One can also consider a composition in the shape of foam or in the form of compositions for aerosol also including a propellant agent under pressure. Cosmetic compositions may also be for orodental use, for example, toothpaste. In that case, the compositions may contain the usual adjuvants and additives for compositions for oral use and, in particular, surfactants, thickening agents, moisturizing agents, polishing agents such as silica, various active substances such as fluorides, particularly sodium fluoride, and, possibly, sweetening agents such as saccharin sodium.

The compositions according to the present invention may be in the form of solution, dispersion, emulsion, paste, or powder. They may be included individually or as a premix in vehicles such as macro-, micro-, or nanocapsules, macro-, micro- or, nanospheres, liposomes, oleosomes or chylomicrons, macro-, micro-, or nanoparticles or macro-, micro or nanosponges. They may also be adsorbed on organic polymer powders, talcs, bentonites, or other inorganic supports. Polypeptides of present invention as well as cosmetic and dermopharmaceutical compositions containing the same, may be used in any form whatsoever, or in a form bound to or incorporated in or absorbed in or adsorbed on macro-, micro-, and nanoparticles, or macro-, micro-, and nanocapsules, for the treatment of textiles, natural or synthetic fibres, wools, and any materials that may be used for clothing or underwear for day or night intended to come into contact with the skin, such as tights, underclothes, handkerchiefs, or cloths, to exert their cosmetic effect via this skin/textile contact and to permit continuous topical delivery.

IV. METHODS FOR TREATING KERATINOUS TISSUE CONDITION

The present invention also covers use of one or more polypeptides of the general formula (I), and use of cosmetic and dermopharmaceutical composition containing one or more of said polypeptides, as an active in or for the preparation of pharmaceutical, preferably cosmetic or dermopharmaceutical composition, with the objective of an anti-age or anti-ageing treatment, in particular in order to treat and/or prevent and/or ameliorating the phenomena of cutaneous aging, such as wrinkles, and/or to improve the appearance of the skin.

The polypeptides according to the present invention and the compositions comprising at least one of said polypeptides are useful for regulating a number of mammalian keratinous tissue conditions. Such regulation includes prophylactic and therapeutic regulation. More specifically, such regulation means preventing, retarding, ameliorating, reducing and/or treating at least one sign of skin aging.

The polypeptides in accordance with the present invention, when provided in formulations, are provided in an amount which is effective to treat at least one sign of skin aging. The phrase "to treat at least one sign of skin aging" as used herein means that the polypeptide provides an objectively measurable increase in its effect on some aspect of aging when used topically and applied to skin in need of treatment in an effective amount. This can be, for example, a greater reduction in wrinkles, a reduction of stretch marks, a reduction of dark circles under the eyes, increased potency, the ability to stimulate or inhibit at least one biochemical process within the skin to a greater degree, and the like. For example, polypeptides and compositions according to the present invention are useful to increase the expression of the extracellular matrix proteins, such as collagen I, collagen IV, elastin, hyaluronic acid and/or fibronectin synthesis more particularly to exhibit collagen I synthesis, and/or collagen IV synthesis and/or fibronectin synthesis when applied to skin cells.

Regulating keratinous tissue condition involves topically applying to the keratinous tissue, for example a portion of human skin, a safe and effective amount of a composition of the present invention for a period of time at least sufficient to provide the expected regulation. This means that the content and/or concentration of the polypeptide, according to the invention, in the composition is sufficient that when the composition is applied with normal frequency and in a normal amount, the composition can result in the treatment and/or prevention and/or regulation of skin condition, including visible and/or tactile discontinuities in skin. This amount of polypeptides may vary depending upon the type of product, which of the signs of aging are to be addressed and the like.

The present invention can also be used to manufacture a medicament capable of prophylatically or therapeutically regulating a skin condition including signs of aging, in particular wrinkles, dark circles and stretch marks. This includes delaying, minimizing or preventing visible or tactile discontinuities.

The present invention also relates to a method of reducing at least one sign of aging, more particularly wrinkles, consisting in applying the composition such as defined previously, to the skin in need of such treatment for a period of time at least sufficient to provide a reduction in at least one sign of aging of that portion of human skin.

The present invention also relates to a method of reducing stretch marks consisting in applying the composition such as defined previously, to the skin in need of such treatment for a period of time at least sufficient to provide a reduction in the visible signs of stretch marks of that portion of human skin.

The present invention also relates to a method of reducing dark circles under the eyes, consisting in applying the composition such as defined previously, to the skin in need of such treatment for a period of time at least sufficient to provide a reduction in the visible signs of dark circles under the eyes.

V. EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. As an illustration of the invention, several cosmetic formulae will be cited. The formulae are representative of, but do not restrict, the invention.

Example 1

Increase in Synthesis of Collagen I, Collagen IV and Fibronectin: In Vitro

Products: Pal-KTFK (SEQ ID NO: 7), Ela-KTAK (SEQ ID NO: 9) and Ela-KTFK (SEQ ID No: 8) were tested from 2 to 6 ppm, and Pal-KAvaK was tested from 1 to 4 ppm. Solvent=DMSO 0.08%. TGF-beta1 $10^{-6}$%, was the positive control for collagen I and fibronectin studies.

Principle of the study: Normal Human Dermal Fibroblasts (NHDF) were cultivated in an appropriate culture medium (i.e. complete DMEM with fetal calf serum). After cell anchorage, cell layers were rinsed with saline buffer and contact with molecules to be tested were performed in a complete DMEM without fetal calf serum. This medium contained ascorbate (sodium salt) and beta-aminopropionitrile, monofumarate. After 3 days of incubation, supernatants were collected and frozen. Survival was estimated on cell layer using a fluorescent probe. Collagen I was estimated using an original direct ELISA method, Fibronectin and Collagen IV were estimated using ELISA commercial kits.

Results: Statistical analysis were performed on Collagen I data (n=5/assay) or fibronectin data (n=5/assay) or Collagen IV data (n=5/assay). Results obtained with molecules were compared to negative control. All data are in ng/10E6 cells. A Student t test for non paired values was used; significativity was obtained if $p<0.05$ or $p<0.01$.

TABLE 1

Effect of Pal-KAvaK on NHDF's Collagen I, fibronectin and collagen IV synthesis. Results are in percent compared to the negative control. Variation of dermal macromolecular proteins synthesis (in % of negative control)

| Product | Concent. | Collagen I (mean) | Fibronectin (mean) | Collagen IV (mean) |
|---|---|---|---|---|
| TGF-beta | 10 ppb | 27 | 124 | 12 |
| Pal-KAvaK | 1 ppm | 1 | 14 | 8 |
|  | 2 ppm | 14 | 15 | 9 |
|  | 4 ppm | 49 | 54 | 23 |

The TGFbeta always shows a significant increase in Collagen I and fibronectin synthesis demonstrating that the cells had responded correctly to stimulation. The peptide PalKAvaK shows an increase of collagen I, Collagen IV and fibronectin synthesis for 4 ppm.

TABLE 2

Effect of Ela-KTAK (SEQ ID NO: 9) on NHDF's Collagen I and fibronectin synthesis. Results are in percent compared to the negative control. Variation of dermal macromolecular proteins synthesis (in % of negative control)

| Product | Concent. | Collagen I (mean) | Fibronectin (mean) |
|---|---|---|---|
| TGF-beta | 10 ppb | 85 | 85 |
| Ela-KTAK | 2 ppm | 6 | 16 |
| (SEQ ID NO: 9) | 4 ppm | 18 | 32 |
|  | 6 ppm | 45 | 31 |

The TGFbeta always shows a significant increase in Collagen I and fibronectin synthesis demonstrating that the cells had responded correctly to stimulation. The peptide Ela-KTAK (SEQ ID NO: 9) shows an increase of fibronectin and collagen I synthesis at 4 ppm and 6 ppm respectively.

TABLE 3

Effect of Ela-KTFK (SEQ ID NO: 8) and Pal-KTFK (SEQ ID NO: 7) on NHDF's Collagen I, fibronectin and collagen IV synthesis. Results are in percent compared to the negative control. Variation of dermal macromolecular proteins synthesis (in % of negative control)

| Product | Concent. | Collagen I (mean) | Fibronectin (mean) | Collagen IV (mean) |
|---|---|---|---|---|
| TGF-beta | 10 ppb | 45 | 87 | — |
| Ela-KTFK | 2 ppm | 6 | 10 | 10 |
| (SEQ ID NO: 8) | 4 ppm | 19 | 25 | 7 |
|  | 6 ppm | 49 | 42 | 7 |
| Pal-KTFK | 2 ppm | 3 | 12 | 10 |
| (SEQ ID NO: 7) | 4 ppm | 38 | 36 | 24 |
|  | 6 ppm | 81 | 55 | 36 |

The TGFbeta always shows a significant increase in Collagen I synthesis demonstrating that the cells had responded correctly to stimulation. The peptide Ela-KTFK (SEQ ID NO: 8) shows a significant increase in collagen I and in fibronectin synthesis at 6 ppm. The peptide Pal KTFK (SEQ ID NO:7) shows an increase in collagen I, fibronectin and collagen IV synthesis at 6 ppm, which seems to be the maximal concentration accepted by the cells.

Example 2

Anti-Wrinkle Night Cream

| PRODUCT | INCI name | % |
|---|---|---|
| PART A |  |  |
| H₂O |  | qsp 100 |
| Ultrez 10 | Carbomer | 0.15 |
| PART B |  |  |
| Glycerine | Glycerin | 3.50 |
| PART C |  |  |
| Volpo S 2 | Steareth 2 | 0.40 |
| Crodafos CES | Cetearyl alcohol dicetyl phosphate & ceteth 10 phosphate | 4.00 |
| DC 345 | Cyclohexasiloxane | 2.00 |
| Crodamol OSU | Dioctyl succinate | 7.00 |
| Volpo S 10 | Steareth 10 | 1.20 |
| Nipastat | Mixed parabens | 0.30 |
| PART D |  |  |
| Sorbate | Sorbate | 0.10 |
| PART E |  |  |
| H2O |  | 2.50 |
| NaOH 38% | Sodium hydroxyde | 0.30 |
| PART F |  |  |
| Perfume | Fragrance | 0.10 |
| PART G |  |  |
| Peptide solution* |  | 3.00 |

Peptide solution*: a stabilised aqueous solution containing 100 ppm of Pal-Lys-Ava-Lys in water/glycerine/carbopol mixture.

This emulsion is prepared in the following way: Part A: disperse Ultrez 10 in water and let it swell for 20 minutes, then add Part B; heat to 75° C. Heat Part C separately to 75° C. Mix the two phases under stirring, homogenise, add Part D, neutralise with Part E, cool until reaching 30° C., then add Part F and Part G, adjust pH to ~6 with NaOH.

The resulting emulsion should be well suited for fragile, aged skin, to improve fine lines, wrinkles, and dryness, reduce redness and irritation.

Example 3

Anti-Wrinkle Cream with Skin Whitening Activity

| PRODUCT | INCI name | % |
|---|---|---|
| Water Deionised | | qs 100 |
| Carbomer | — | 0.10 |
| Potassium Sorbate | — | 0.10 |
| Transcutol | — | 3.00 |
| Glycerin | | 8.00 |
| Volpo S2 | Steareth 2 | 0.60 |
| Crodafos CES | Cetearyl Alcohol (and) Dicetyl Phosphate (and) Ceteth 10 Phosphate | 4.00 |
| DC 344 | Cyclomethicone | 2.00 |
| Crodamol GTCC | Caprylic/Capric Triglyceride | 10.00 |
| Crill 3 | Sorbitan Stearate | 1.60 |
| Vitamin E | | 0.50 |
| Mixed Parabens | | 0.30 |
| Sodium Hydroxide 30% | | 0.35 |
| Water Deionised | | 3.50 |
| 2PO4-L ascorbic acid tri Na | | 0.33 |
| Pal-Lys-Ava-Lys | | 0.0006 |
| ETIOLINE ® | Glycerine (and) Butylene Glycol (and) Arcostaphylus uva leaf extract and Mitracarpus Scaber extract*) | 3.00 |

*ETIOLINE ® is a skin lightening ingredient sold by SEDERMA (WO98/05299). This formulation can be made according to the procedures generally outlined in Example 2.

Example 4

Anti Stretch-Mark Cream

| PRODUCT | INCI name | % |
|---|---|---|
| Part A | | |
| Water Deionised | | qs 100 |
| Ultrez 10 | Carbomer | 0.40 |
| Part B | | |
| Glycerin | | 5.00 |
| Phenova | Phenoxyethanol (and) Mixed Parabens | 0.80 |
| Part C | | |
| Crodamol OP | Ethylhexyl Palmitate | 4.00 |
| Crodacol CS90 | Cetearyl alcohol | 0.50 |
| Crodamol ML | Myristyl Lactate | 0.30 |
| Crillet 1 | Polysorbate 20 | 1.00 |
| Part D | | |
| Pemulen TR2 | Acrylates/C 10-30 Alkyl Acrylate (and) Crosspolymer | 0.20 |
| DC 345 | Cyclomethicone | 2.00 |
| Part E | | |
| Potassium Sorbate | | 0.10 |

-continued

| PRODUCT | INCI name | % |
|---|---|---|
| Part F | | |
| Water | | 6.00 |
| Sodium Hydroxide 38% | | 0.60 |
| Part G | | |
| MATRIXYL ® 3000 | | 3.00 |
| Peptide SOLUTION* | | 2.00 |
| Darutoside | Siegesbeckia Orientalis Extract | 2.00 |

Darutoside ™ is an ingredient sold by SEDERMA for the treatment of stretch marks. MATRIXYL ® 3000 is sold by SEDERMA (Us2004/013667) and contains: butylene glycol, carbomer, polysorbate-20, N-Palmitoyl-Gly-Gln-Pro-Arg (SEQ ID NO: 15) and N-Palmitoyl-Gly-His-Lys. The concentration of the tetrapeptide is 0.005% (w/w) and the concentration of the tripeptide is 0.01%, thus in the example cited, the amount of tripeptide is 0.0003% and of tetrapeptide 0.00015%.

This emulsion is prepared in the following way: Part A: disperse Ultrez 10 in water and let it swell for 20 minutes, then add Part B; heat to 75 Co. Heat Part C separately to 75° C. Mix the two Parts under stirring, homogenise, add Part D, neutralise with Part E, cool until reaching 30° C., then add Part F and Part G, adjust pH to ~6 with NaOH.

Example 5

Moisturising Face Gel

| PRODUCT | INCI name | % |
|---|---|---|
| Part A | | |
| Ultrez 10 | Carbomer | 0.20 |
| Water Deionised | | qs 100 |
| Part B | | |
| Glycerin | | 3.00 |
| Phenova | Phenoxyethanol (and) Mixed Parabens | 0.80 |
| Part C | | |
| Crillet 1 | Polysorbate 20 | 0.50 |
| Part D | | |
| Potassium Sorbate | | 0.10 |
| Part E | | |
| Pemulen TR1 | Acrylates/C10-30 Alkyl Acrylate Crosspolymer | 0.20 |
| DC 345 | Cyclomethicone | 3.00 |
| Part F | | |
| Water | | 4.00 |
| Sodium Hydroxide 38% | | 0.40 |
| Pal-Lys-Thr-Phe-Lys (SEQ ID NO: 7) | | 0.0003 |
| MOIST-24 ® | Imperata Cylindrica (root) Extract (and) water (and) Glycerin (and) PEG-8 (and) Carbomer | 5.00 |

MOIST-24 ™ is a moisturising plant extract sold by SEDERMA (WO01/62218). This formulation can be made according to the procedures generally outlined in Example 4.

Example 6

Anti-Age Soothing Day Cream

| PRODUCT | INCI name | % |
|---|---|---|
| Water Deionised | | qs 100 |
| Ultrez 10 | Carbomer | 0.20 |
| Part B | | |
| Potassium Sorbate | | 0.10 |
| Part C | | |
| Butylene Glycol | | 2.00 |
| Phenova | Phenoxyethanol (and) Mixed Parabens | 0.80 |
| Part D | | |
| Crill 3 | Sorbitan Stearate | 1.00 |
| Crillet 3 | Polysorbate 60 | 2.50 |
| DC 200 | Dimethicone | 2.50 |
| Crodamol TN | Isotridetyl Isononanoate | 5.00 |
| Crodamol GTCC | Caprylic/Capric Triglyceride | 5.00 |
| Crodamol SS | Cetyl Esters | 1.00 |
| Super Hartolan | Lanolin Alcohol | 0.50 |
| Super Sterol Ester | C10-C30 Cholesterol/Lanosterol esters | 0.30 |
| Crodacol CS90 | Cetearyl Alcohol | 3.00 |
| Part E | | |
| Water Deionised | | 2.50 |
| Sodium Hydroxide 38% | | 0.25 |
| Part F | | |
| Ela-Lys-Thr-Phe-Lys (SEQ ID NO: 8) | | 0.00009 |
| CALMOSENSINE ® | Butylene Glycol (and) water (and) Laureth-3 (and) Hydroxyethylcellulose (and) Acetyl-Dipeptide-1-cetylester | 4.00 |

Calmosensine ® is an analgesic peptide offered by SEDERMA (WO98/07744). This formulation can be made according to the procedures generally outlined in Example 4.

Example 7

Cream for Mature Skin with Isoflavones

| PRODUCT | INCI name | % |
|---|---|---|
| Part A | | |
| Ultrez 10 | Carbomer | 0.20 |
| Water Deionised | | qs 100 |
| Part B | | |
| Glycerin | | 3.50 |
| Part C | | |
| Potassium Sorbate | | 0.10 |
| Part D | | |
| Volpo S10 | Steareth 10 | 1.50 |
| Crodafos CES | Ceterayl Alcohol Dicetyl Phosphate (and) Ceteth-10 Phosphate | 3.50 |
| DC 200 | Dimethicone | 2.00 |
| Crodamol OSU | Diethylhexyl Succinate | 7.00 |
| Mixed Parabens | | 0.30 |
| Crill 3 | Sorbitan Stearate | 0.40 |
| Part E | | |
| Sodium Hydroxide 38% | | 0.20 |
| Water Deionised | | 4.00 |
| Part F | | |
| STEROCARE ™ | Trifolium Pratense (Clover) Flower Extract (and) Glycerin (and) Butylene Glycol (and) Lecithin | 3.00 |

-continued

| PRODUCT | INCI name | % |
|---|---|---|
| Ela-Lys-Thr-Ala-Lys (SEQ ID NO: 9) | | 0.001 |
| Ascorbic acid | | 0.1 |

Sterocare ® is offered by SEDERMA as an active ingredient for mature skin (FR2769502, WO99/18927). This formulation can be made according to the procedures generally outlined in Example 4.

Example 8

Hair Tonic Against Hair Loss

| PRODUCT | INCI name | % |
|---|---|---|
| Part A | | |
| Water deionised | | Qs 100 |
| Part B | | |
| Mixed Parabens | | 0.14 |
| Butylene Glycol | | 2.00 |

-continued

| PRODUCT | INCI name | % |
| --- | --- | --- |
| Part C | | |
| PROCAPIL ® | Butylene Glycol (and) Water (Aqua) (and) PPG-26-Buteth-26 (and) PEG-40 Hydrogenated Castor Oil (and) Apigenin (and) Oleanolic Acid (and) Biotinoyl Tripeptide-1 | 3.00 |
| Pal-Lys-Ava-Lys | | 0.0005 |
| Pal-Gly-Gln-Pro-Arg (SEQ ID NO: 15) | | 0.0003 |
| Ethanol | | 10.00 |
| Part D | | |
| Crillet 1 | Polysorbate 20 | 1.50 |
| Fragrance | | 0.10 |

PROCAPIL ® (Us11/097,666) is offered by Sederma as an active ingredient fighting against hairloss.

Method: weigh Part A. Weigh and melt Part B. Allow Part B to cool. Mix Part B with Part A with helix stirring. Mix Part C and add it to Part A+B. Add Part D to Part A+B+C.

Example 9

Lotion to Treat Dark Circles Under the Eyes

| PRODUCT | INCI name | % |
| --- | --- | --- |
| Part A | | |
| Ultrez 10 | Carbomer | 0.20 |
| Water Deionised | | qs 100 |
| Part B | | |
| Glycerin | | 3.00 |
| Part C | | |
| Potassium Sorbate | | 0.10 |
| Part D | | |
| Volpo S 10 | Steareth 10 | 1.50 |
| Crodafos CES | Ceterayl Alcohol Dicetyl Phosphate (and) Ceteth-10 Phosphate] | 3.00 |
| DC 200 | Dimethicone | 2.00 |
| Crodamol OSU | Diethylhexyl Succinate | 5.00 |
| Mixed Parabens | | 0.30 |
| Crill 3 | Sorbitan Stearate | 0.40 |
| Part E | | |
| Sodium Hydroxide 38% | | 0.20 |
| Water Deionised | | 4.00 |
| Part F | | |
| Water | | 10.0 |
| Ela-Lys-Ala-Tyr-Lys (SEQ ID NO: 10) | | 0.0005 |
| N-Hydroxysuccinimide | | 0.001 |
| Passion Flower extract | | 2.00 |

This emulsion is prepared in the following way: Part A: disperse Ultrez 10 in water and let it swell for 20 minutes, then add Part B; heat to 75 Co. Heat Part D separately to 75° C. Mix the two Parts under stirring, homogenise, add Part C, neutralise with Part E, cool until reaching 30° C., then add Part F and adjust pH to −6 with NaOH.

The combination of these ingredients is destined to treat dark circles based on the fact that the iron chelator N-Hydroxysuccinimide and the Passion Flower extract (containing chrysin) act together to eliminate haemoglobin residues, the peptides resynthesise tissue and thicken the skin. N-Hydroxysuccinimide can be replaced by Deferoxamine, EDTA, NTA, hydroxamic acids or other iron chelators in the appropriate amounts for efficient iron chelation. Passion Flower Extract can be replaced by Berberine, chrysine or similar flavonoids for the same purpose of stimulating the elimination of bilirubine.

Example 10

Anti-Stretchmark Gel

| PRODUCT | INCI name | % |
| --- | --- | --- |
| Part A | | |
| Water Deionised | | qs100 |
| Part B | | |
| Butylene Glycol | | 5.00 |
| Phenova | Phenoxyethanol (and) Mixed Parabens | 0.80 |
| Part C | | |
| Crill 3 | Sorbitan Stearate | 1.20 |
| Crillet 3 | Polysorbate 60 | 3.00 |
| DC 200 | Dimethicone | 2.00 |
| Crodamol IPM | Isopropyl Myristate | 5.00 |
| Crodamol W | Stearyl Heptanoate | 0.30 |
| Crodamol GTCC | Caprylic/Capric Triglyceride | 5.00 |
| Crodacol CS90 | Cetearyl Alcohol | 2.00 |
| Part D | | |
| Carbopol 980 at 2% | Carbomer | 10.00 |
| Part E | | |
| Potassium Sorbate | | 0.10 |
| Part F | | |
| Water Deionised | | 2.00 |
| Sodium Hydroxide | | 0.20 |
| Part G | | |
| Water | | 10.0 |
| Pal-Lys-Thr-Phe-Lys (SEQ ID NO: 7) | | 0.0003 |
| Rutin | | 0.10 |
| Bowman Birk Inhibitor | | 0.0001 |

This gel can be prepared in the following way: Homogenize Part B and pour it into Part A. Heat Part (A+B) to 75° C. Heat Part C and Part D to 75° C. Pour Part C into Part (A+B) with helix stirring; then, pour Part D into Part (A+B+C). Add Part F and Part E. Pour Part G at about 35° C. Rutin and Bowman Birk Inhibitor contribute to antistretchmark activity by allowing tissue regeneration, inhibiting protein breakdown and strengthening the crosslinks of collagen fibers.

They can be replaced by similar flavonoids or protease enzyme inhibitors respectively.

Example 11

Face Lift and Firming Cream

| PRODUCT | INCI name | % |
|---|---|---|
| Part A | | |
| Ultrez 10 | Carbomer | 0.40 |
| Water deionised | | qsp100 |
| Part B | | |
| Glycerin | | 5.00 |
| Mixed parabens | | 0.20 |
| Part C | | |
| Crodamol GTCC | Caprylic/Capric Triglycerides | 4.00 |
| Crodacol CS90 | Cetearyl Alcohol | 0.50 |
| Crodamol ML | Myristyl Lactate | 0.30 |
| Crillet 1 | Polysorbate 20 | 1.00 |
| Part D | | |
| Cyclomethicone | | 2.00 |
| Pemulen TR2 | Acrylates/C 10-30 Alkyl Acrylate Cross Polymer | 0.20 |
| Part E | | |
| Potassium Sorbate | | 0.10 |
| Part F | | |
| Water deionised | | 6.00 |
| Sodium hydroxide 30% | | 0.60 |
| Part G | | |
| PEPTIDE SOLUTION* with Pal-Lys-Ava-Lys | | 4.00 |
| LIPOCARE | Butylene Glycol (and) PEG-8 (and) Bupleurum falcatum Extract (and) Caffeine (and)Coenzyme A | 2.00 |
| KOMBUCHKA | Saccharomyces/Xylinum Black Tea Ferment (and) Glycerin (and) Hydroxyethylcellulose | 3.00 |

KOMBUCHKA ® is offered by SEDERMA as an active improving skin radiance (WO2004/012650) and LIPOCARE ™ is offered by SEDERMA as a firming active (WO98/43607)

Method: Part A: sprinkle Ultrez 10 in the water and let swell for 15 minutes. Heat Part B until dissolution and add it to Part A. Weigh Part C and heat to 75° C. in water-bath. Heat Part (A+B) to 75° C. in water-bath. Weigh Part D. Add Part C to Part (A+B) and Part D extemporaneously. Then add part E. Neutralize with Part F at around 45° C. Finally, add Part G. Homogenize carefully. pH: 5.90

Example 12

Treatment for Dark Circles and Puffy Eyes

| PRODUCT | INCI name | % |
|---|---|---|
| Part A | | |
| Water | | qsp 100 |
| Ultrez 10 | Carbomer | 0.20 |
| Part B | | |
| Glycerin | | 5.00 |
| Preservatives | | qs |
| Part C | | |
| Hydroxyethylcellulose | | 0.20 |
| Part D | | |
| Pemulen TR2 | Acrylates/C10-30 Alkyl Acrylate Crosspolymer | 0.20 |
| Crodamol CAP | Cetearyl Ethylhexanoate | 6.00 |
| Part E | | |
| Potassium sorbate | Potassium Sorbate | 0.10 |
| Part F | | |
| Water deionised | | 4.00 |
| NaOH 30% | Sodium Hydroxide | 0.46 |
| Part G | | |
| Quercetin | | 0.0005 |
| Deferoxamin | | 0.015 |
| Pal-Lys-Abu-Lys | | 0.001 |
| EYELISS ® | Water (and) Glycerin (an) Hesperidin Methyl Chalcone (and) Stearth -20 (and) Dipeptide-2 (and) Palmitoyl Tetrapeptide-3 | 3.00 |
| Crillet 1 | Polysorbate 20 | 0.50 |
| Part H | | |
| Fragrance | | qs |

EYELISS ® is offerered by SEDERMA as an active treating puffy eyes (WO03/068141)

This gel is prepared in the following way: Part A: Disperse Ultrez 10 in water and let it swell for minutes. Part B: Heat glycerin at 60° C., dissolve preservatives; cool at 40° C. Add Part C to Part B, homogenize; then add Part (B+C) to Part A, under stirring. Wait one hour. Add Part D, then Part E to (A+B+C). Adjust pH with Part F, wait one hour. Add Part G, homogenize, and then add part H.

By applying twice a day this gel around the eyes, one can observe a reduction in the bags under the eyes, a relieving congestion effect and an attenuation of the dark circles.

Example 13

Protective Lip Balm

| PRODUCT | INCI name | % |
|---|---|---|
| Castor oil | Castor (Ricinum communis) Oil | 5.00 |
| Crodamol PTIS | Pentaerythrityl Tetraisostearate | qsp 100 |
| Syncrowax HRC | Tribehenin | 6.00 |
| Syncrowax ERLC | C18-36 Acid Glycol Ester | 6.00 |
| Novol | Oleoyl Alcohol | 9.00 |
| Crodacol C90 | Cetyl Alcohol | 4.00 |
| Super Sterol Ester Lanosterol Esters | C10-30 Cholesterol/ | 2.00 |
| Carnauba wax | Carnauba (Copernicia cerifera) wax | 5.00 |
| Paraffin | Paraffin | 4.00 |
| Part B | | |
| MAXI-LIP | Octyl Palmitate-Tribehenin-Sorbitan Isostearate-Palmitoyl-Oligopeptide | 1.00 |
| Ela-Lys-Phe-Tyr-Lys (SEQ ID NO: 11) | | 0.004 |
| Mixed Parabens | | Qs |
| Part C | | |
| Crill 6 | Sorbitan Isostearate | 7.00 |
| Polyolprepolymer 14 | PPG-51/SMDI Copolymer | 5.00 |
| Perfume | | qs |

This balm is prepared by the following way: Part A: Dissolve the ingredients at 80° C.; homogenize. Add Phase B, then Phase C; homogenize and pour.

Example 14

Reconstructive Night Cream

| PRODUCT | INCI name | % |
|---|---|---|
| Part A | | |
| H2O | | Qsp100 |
| Ultrez 10 | Carbomer | 0.20 |
| Part B | | |
| Glycerin | Glycerin | 5.00 |
| Part C | | |
| Volpo S 2 | Steareth 2 | 0.60 |
| Crodafos CES | Cetearyl Alcohol Dicetyl Phosphate & Ceteth 10 Phosphate | 4.00 |
| Super Sterol Ester | C10 C30 Cholesterol Ester | 0.30 |
| Crodamol OSU | Dioctyl Succinate | 7.00 |
| Crodamol CAP | Cetearyl Ethylhexanoate | 3.00 |
| Methyl Paraben | Methyl Paraben | 0.30 |
| Crill 3 | Sorbitan Stearate | 1.60 |
| Crodamol STS | PPG 3 Benzyl Ether Myristate | 2.00 |
| Part D | | |
| Sorbate | Potassium Sorbate | 0.10 |
| Part E | | |
| NaOH 30 % | Sodium Hydroxyde | 0.35 |
| H2O | | 3.50 |
| Part F | | |
| CHRONODYN ™ PEPTIDE SOLUTION* | Euglena gracilis extract | 3.00 |
| Pal-Lys-Ava-Lys | | 3.00 |
| Part G | | |
| Perfume | Fragrance | 0.10 |

Method: Sprinkle Ultrez 10 in water and let swell for 30 minutes. Add Part B. After heating each part, add Part (A+B) to Part C with helix stirring during 1 hour. Add Part D. Add Part E around 45° C. Add Part F and G around 35° C. pH=5.80.

Example 15

Liquid Foundation

| PRODUCT | INCI name | % |
|---|---|---|
| Part A | | |
| Deionized water | | qsp 100 |
| KOH 10% | Potassium hydroxide | 1.30 |
| Crillet 4 NF | Polysorbate 80 | 0.10 |
| Part B | | |
| Titanium Dioxide | | 6.00 |
| Talc | | 3.05 |
| Yellow Iron Oxide | | 1.80 |
| Red Iron Oxide | | 1.00 |
| Black Iron Oxide | | 0.15 |

| PRODUCT | INCI name | % |
|---|---|---|
| Part C | | |
| Propylene glycol | | 4.00 |
| Magnesium Aluminum Silicate | | 1.00 |
| Part D | | |
| Propylene glycol | | 2.00 |
| Sodium Carboxymethylcellulose | | 0.12 |
| Part E | | |
| Cromollient DP3-A | Di-PPG-3 Myristyl Ether Adipate | 12.00 |
| Crodamol ISNP | Isostearyl Neopentanoate | 4.00 |
| Crodafos CS 20 Acid | Cetearyl Alcohol (and) Ceteth-20 Phosphate (and) Dicetyl Phosphate | 3.00 |
| Volpo S-10 | Steareth-10 | 2.00 |
| Crodacol C-70 | Cetyl Alcohol | 0.62 |
| Volpo S-2 | Steareth-2 | 0.50 |
| Ceramide 2 | | 0.10 |
| Pal-Lys-βAla-Lys | | 0.04 |
| Part F | | |
| Germaben II | Propylene glycol (and) Diazolidinyl Urea (and) Methylparaben (and) Propylparaben) | 1.00 |

Using a tared 1500-ml beaker, combine part A and begin homogenizing. In an Osterizer, pre-mill part B (3× for 15 seconds) until pigments are well blended. Add part B to part A and homogenize until pigments are dispersed evenly. Begin heating. Prepare a slurry with part C ingredients and add to part A/B. Bring heat up to 85° C. and maintain temperature of 85-900° C. for 10 minutes. Remove heat. Prepare a slurry with part D ingredients and add to part A/B/C at 77° C. Homogenize until uniform and smooth. Check weight and add water to compensate for any loss, plus 20 grams (per kilogram). Continue mixing and bring heat back up to 77° C. Combine part E separately and heat to 77° C. Add to main mixture and maintain 77-80° C. temperature for 10 minutes. Remove heat. At 50° C., add part F. Check for water loss again. Adjust pH to 7.5 with KOH, if necessary. Homogenizing until temperature reaches 35° C.

Example 16

Anti-Ageing Gel for Men

| PRODUCT | INCI name | % |
|---|---|---|
| Part A | | |
| Ultrez 10 | Carbomer | 0.20 |
| Water deionised | | qsp 100 |
| Part B | | |
| Glycerin | | 5.00 |
| Methyl paraben | | 0.20 |
| Part C | | |
| Hydroxyethyl Cellulose | | 0.20 |
| Part D | | |
| Pal-Lys-Aca-Lys | | 0.10 |
| Ascorbyl phosphate | | 0.01 |
| Crillet 1 | Polysorbate 20 | 0.50 |

| PRODUCT | INCI name | % |
|---|---|---|
| Part E | | |
| Pemulen TR2 | Acrylates/C 10-30 Alkyl Acrylate Cross Polymer | 0.20 |
| DC 200 | Dimethicone | 2.00 |
| Part F | | |
| Potassium Sorbate | | 0.10 |
| Part G | | |
| Water deionised | | 4.00 |
| Sodium Hydroxide 30% | | 0.40 |
| Part H | | |
| Fragrance | | 0.10 |

Part A: sprinkle Ultrez 10 in the water and allow to swell for 15 minutes. Melt Part B to 60° C. and allow to cool to around 40° C. Mix Part C with Part B, homogenize. Add Part B+C to Part A with helix stirring and allow to swell for 1 hour. Heat Part D to 80° C. Heat Part A+B+C to 80° C. Pour Part D into Part A+B+C with Staro stirring (3000 rpm). Mix part E and, extemporaneously, add it to the previous part. Then add part F at 75° C. and allow to swell for 1 hour. Neutralize with Part G at 50° C. Add Part H at 35° C. Mix well.

The invention claimed is:

1. A compound selected from the group consisting of Pal-Lys-Thr-Phe-Lys (SEQ ID NO:7), Ela-Lys-Thr-Phe-Lys (SEQ ID NO:8), Ela-Lys-Thr-Ala-Lys (SEQ ID NO:9), Pal-Lys-Ava-Lys, Ela-Lys-Ala-Tyr-Lys (SEQ ID NO:10), Ela-Lys-Phe-Tyr-Lys (SEQ ID NO:11), Pal-Lys-βAla-Lys, Pal-Lys-Abu-Lys and Pal-Lys-Aca-Lys.

2. A cosmetic or dermopharmaceutical composition comprising
a) at least one compound according to claim 1 and
b) a dermatologically acceptable carrier.

3. The cosmetic or dermopharmaceutical composition according to claim 2 wherein said compound is present at a concentration between 0.00001% (w/w) and 15% (w/w) by weight of the composition.

4. The cosmetic or dermopharmaceutical composition according to claim 2 further comprising one or more skin anti-aging agent, anti-wrinkle agent, anti-atrophy agent, or an anti-oxidant/radical scavenger.

5. The cosmetic or dermopharmaceutical composition according to claim 2 further comprising at least one skin care active or additional ingredient.

6. The cosmetic or dermopharmaceutical composition according to claim 2 wherein said compound is present at a concentration between 0.0001% (w/w) and 0.1% (w/w) by weight of the composition.

7. The compound of claim 1 wherein said compound is Pal-Lys-Thr-Phe-Lys (SEQ ID NO:7) or Pal-Lys-Ava-Lys.

* * * * *